US008546638B2

(12) United States Patent
Zhou et al.

(10) Patent No.: US 8,546,638 B2
(45) Date of Patent: Oct. 1, 2013

(54) ABSORBENT ARTICLE HAVING IMPROVED SIGNAL MEMBER

(75) Inventors: Peiguang Zhou, Appleton, WI (US); Andrew Mark Long, Appleton, WI (US); Dave Allen Soerens, Neenah, WI (US); Kaiyuan Yang, Cumming, GA (US); James Hongxue Wang, Neenah, WI (US); Xuedong Song, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 518 days.

(21) Appl. No.: 12/646,743

(22) Filed: Dec. 23, 2009

(65) Prior Publication Data
US 2011/0152816 A1 Jun. 23, 2011

(51) Int. Cl.
*A61F 13/42* (2006.01)
(52) U.S. Cl.
USPC .......................................... 604/361
(58) Field of Classification Search
USPC .................................. 604/361, 362
See application file for complete search history.

(56) References Cited

U.S. PATENT DOCUMENTS

| | | | | |
|---|---|---|---|---|
| 5,649,914 A | * | 7/1997 | Glaug et al. ................. | 604/361 |
| 5,681,298 A | | 10/1997 | Brunner et al. | |
| 5,702,377 A | | 12/1997 | Collier, IV et al. | |
| 6,307,119 B1 | | 10/2001 | Cammarota et al. | |
| 6,464,672 B1 | | 10/2002 | Buckley | |
| 6,716,498 B2 | | 4/2004 | Curro et al. | |
| 6,726,668 B2 | | 4/2004 | Underhill et al. | |
| 6,929,819 B2 | | 8/2005 | Underhill et al. | |
| 6,958,432 B2 | | 10/2005 | Underhill et al. | |
| 7,002,055 B2 | | 2/2006 | Long et al. | |
| 7,083,839 B2 | | 8/2006 | Fish et al. | |
| 7,175,613 B2 | | 2/2007 | Sugiyama et al. | |
| 7,250,548 B2 | | 7/2007 | Weber et al. | |
| 7,297,835 B2 | * | 11/2007 | Olson ........................... | 604/364 |
| 7,632,978 B2 | | 12/2009 | Olson et al. | |
| 2002/0169427 A1 | | 11/2002 | Roe et al. | |
| 2004/0122396 A1 | | 6/2004 | Maldonado et al. | |
| 2004/0254550 A1 | | 12/2004 | Huang et al. | |
| 2005/0107759 A1 | | 5/2005 | Waksmundzki et al. | |
| 2005/0203473 A1 | | 9/2005 | Pesce et al. | |
| 2006/0142714 A1 | | 6/2006 | Jackson et al. | |

(Continued)

FOREIGN PATENT DOCUMENTS
KR     10-2008-0046414 A     5/2008

OTHER PUBLICATIONS

"Graphic Indicators for Training Pants," ISSN 0226-2078, discussion of K-C U.S. Pat. No. 6,307,119, *Medical Textiles*, Apr. 2002, 1 page.

*Primary Examiner* — Susan Su
(74) *Attorney, Agent, or Firm* — Randall W. Fieldhack; Kenya T. Pierre; Bryan R. Rosiejka

(57) ABSTRACT

An absorbent article comprises a signal element having a body-facing surface, a garment-facing surface, a longitudinal direction, a transverse direction and a z-direction. The signal element includes a water-soluble polymeric buffering film and a stimulation material. The water-soluble polymeric buffering film comprises a water-soluble base polymer. In some aspects, the stimulation material comprises a temperature change agent, and the signal element exhibits a surface temperature change of at least +/−2° C. In some aspects, the signal element exhibits a stimulation effect over at least two aqueous insults.

14 Claims, 8 Drawing Sheets

(56) References Cited

U.S. PATENT DOCUMENTS

2007/0233026 A1 10/2007 Roe et al.
2007/0252713 A1 11/2007 Rondoni et al.
2007/0287971 A1 12/2007 Roe et al.
2008/0119812 A1 5/2008 Hurwitz
2008/0147153 A1 6/2008 Quincy et al.
2008/0269703 A1 10/2008 Collins et al.
2009/0054860 A1 2/2009 Young et al.
2011/0152806 A1 6/2011 Zhou et al.

* cited by examiner

ABSORBENT ARTICLE HAVING IMPROVED SIGNAL MEMBER

BACKGROUND

The present invention relates to absorbent articles that include a stimulation material. More specifically, the invention relates to an absorbent article, such as training pants, that provides the wearer with a noticeable change in sensation upon fluid insult.

Absorbent articles, such as children's training pants for example, have been designed with temperature change particles to provide a temperature change sensation upon urination in an attempt to enhance a child's recognition of when urination occurs. As can be appreciated, such recognition can be an important step in the toilet training process. The temperature change sensation can often be the result of the stimulation material being positioned between the topsheet and the absorbent core of the article.

Unfortunately, in certain circumstances, the design of such articles may not be completely satisfactory. For example, the stimulation material included within the article can, in certain instances, be abrasive to the wearer. This abrasiveness can be particularly notable where the stimulation material is positioned close to the wearer's skin in use, which is generally a desirable configuration to maximize the temperature change sensation experienced by the wearer. Moreover, the stimulation material may provide a rapid temperature change sensation, but it may not last as long as desired to assist with the toilet training process.

One attempt to resolve this issue has been to place large quantities of stimulation material, such as 75 wt % sorbitol, into a single layer coform fabric made from 67% by weight polypropylene meltblown fibers and 33% by weight pulp fibers to form a signal element member. However, the cost and complexity of producing such a signaling element can be prohibitively high. For example, the coform process tends to be very complex, and sorbitol tends to be a relatively high cost material. Furthermore, the maximum stimulation effect may nonetheless be reached relatively quickly, such as during or near the first insult, despite the coform fabric.

Thus, there is a need for an absorbent article with an improved signal element that can delay or prolong the effects of the stimulation material, that has the same or a relatively lower cost and/or complexity of manufacture than currently available signal elements, and that can potentially provide a pleasing surface to the wearer.

SUMMARY

In response to the needs discussed above, an absorbent article comprises a signal element having a body-facing surface, a garment-facing surface, a longitudinal direction, a transverse direction and a z-direction. The signal element comprises a water-soluble polymeric buffering film and a stimulation material. The water-soluble polymeric buffering film comprises a water-soluble base polymer. The stimulation material comprises a temperature change agent. In addition, the signal element exhibits a surface temperature change of at least +/−2° C. from a dry state at 23° C. after being completely submerged for 10 seconds in tap water having a temperature of 23° C. In some aspects, the water-soluble base polymer is selected from polyethylene oxide, polyethylene glycol or polyvinyl alcohol. In other aspects, the water-soluble polymeric buffering film further comprises at least one of a plasticizer, a water-solubility control agent or a pH adjustment agent. In still other aspects, the stimulation material is selected from a cooling agent or a warming agent. In yet other aspects, the cooling agent has a heat of solution, hydration, or reaction of −30 to −90 cal/g. In still other aspects, the cooling agent is selected from xylitol, sorbitol or urea. In yet other aspects, the stimulation material is present in the signal element at a basis weight of 50 gsm to 2000 gsm. In yet other aspects, the stimulation material has a solubility of from 0.1 grams to 6 grams of material per gram of water. In still other aspects, the signal element exhibits a stimulation effect for at least 5 minutes after a first aqueous insult according to the Aqueous Insult Procedure. In yet other aspects, the signal element exhibits a stimulation effect during at least two aqueous insults according to the Aqueous Insult Procedure. In still other aspects, the signal element does not completely dissolve until between 5 minutes and 30 minutes after being completely submerged in tap water at 23° C. In yet other aspects, the signal element does not reach a maximum stimulation effect until at least 4 minutes after a first aqueous insult according to the Aqueous Insult Procedure.

In an alternative aspect of the invention, an absorbent article comprises a signal element having a body-facing surface, a garment-facing surface, a longitudinal direction, a transverse direction and a z-direction. The signal element comprises a water-soluble polymeric buffering film and a stimulation material. The water-soluble polymeric buffering film comprises a water-soluble base polymer. In addition, the signal element exhibits a stimulation effect over at least two aqueous insults according to the Aqueous Insult Procedure. In some aspects, the water-soluble base polymer is selected from polyethylene oxide, polyethylene glycol or polyvinyl alcohol. In other aspects, the water-soluble polymeric buffering film further comprises at least one of a plasticizer, a water-solubility control agent or a pH adjustment agent. In still other aspects, the stimulation material is selected from a cooling agent, a warming agent or a pressure change agent. In yet other aspects, the signal element exhibits a stimulation effect for at least 5 minutes after a first aqueous insult according to the Aqueous Insult Procedure. In still other aspects, the signal element exhibits a stimulation effect for at least 20 minutes after a first aqueous insult according to the Aqueous Insult Procedure. In yet other aspects, the signal element does not completely dissolve until between 5 minutes and 30 minutes after being completely submerged in tap water at 23° C. In still other aspects, the stimulation material comprises polymers having acidic functionalities.

Numerous other features and advantages of the present invention will appear from the following description. In the description, reference is made to exemplary embodiments of the invention. Such embodiments do not represent the full scope of the invention. Reference should therefore be made to the claims herein for interpreting the full scope of the invention. In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

FIGURES

The foregoing and other features, aspects and advantages of the present invention will become better understood with regard to the following description, appended claims and accompanying drawings. Unless otherwise denoted, longitudinal cross-section views are taken along a longitudinal centerline.

FIG. 1 representatively illustrates a side view of a pair of training pants with a mechanical fastening system of the pants shown fastened on one side of the training pants and unfastened on the other side of the training pants.

FIG. 2 representatively illustrates a plan view of the training pants of FIG. 1 in an unfastened, stretched and laid flat condition, and showing the surface of the training pants that faces toward the wearer.

Figure 1:
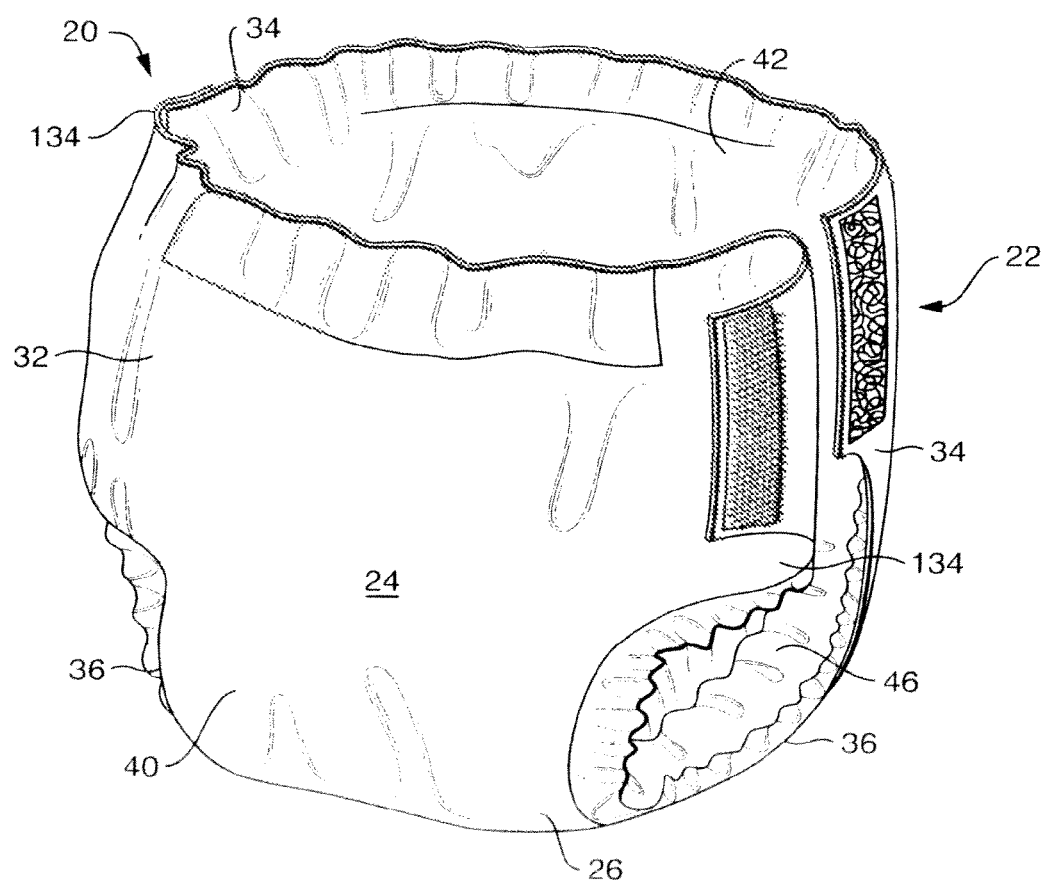

Repeated use of reference characters in the present specification and drawings is intended to represent the same or analogous features or elements of the present invention. The drawings are representational and are not necessarily drawn to scale. Certain proportions thereof may be exaggerated, while others may be minimized.

Test Methods

Unless otherwise noted, all tests are performed at a temp of 23° C. and a relative humidity of 50%.

Particle Size Test

A stack of sieves are used to determine the particle size distribution of a given sample. Thus, for example, a particle that is retained on a sieve with 710 micron openings is considered to have a particle size greater than 710 microns. A particle that passes through a sieve having 710 micron openings and is retained on a sieve having 500 micron openings is considered to have a particle size between 500 and 710 microns. Further, a particle that passes through a sieve having 500 micron openings is considered to have a particle size less than 500 microns.

The sieves are placed in order of the size of the openings with the largest openings on the top of the stack and the smallest openings on the bottom of the stack. Thus, all of the stimulation material associated with a signal element can be weighed and placed into the sieve with the largest openings. Alternatively, if it is desired to determine the particle size or particle size distribution of the stimulation material in only a particular portion of the signal element, only the stimulation material associated with that portion can be weighed and placed into the sieve with the largest openings. U.S. Standard sieves can be used in the sieve stack, including 20 mesh (850 microns), 25 mesh (710 microns), 35 mesh (500 microns), 50 mesh (300 microns) and 170 mesh (90 microns).

The sieve stack is shaken for 10 minutes with a Ro-Tap mechanical Sieve Shaker, Model RX29 available from W.S. Tyler of Mentor, Ohio, or other similar shaking device at standard test conditions. After shaking is complete, the stimulation material retained on each sieve is removed and the weight is measured and recorded. The percentage of particles retained on each sieve is calculated by dividing the weights of the particles retained on each sieve by the initial sample weight.

Particle Distribution Test

The stimulation material distribution within the signal element is measured by way of a photomicrograph, electron micrograph, or similar imaging technique. For example, a Scanning Electron Microscope (JSM-840 from J.E.O.L., Peabody, Mass.) can be used. Cross-sections can be taken in the z-direction by cutting with a fresh straight-edge razor blade, taking care to avoid dragging stimulation material from one area of the signal element to another area of the signal element. Accordingly, a magnified image of the z-directional cross-section of the signal element can be taken. From this image, dimensions of the signal element can be determined, and the distribution of the stimulation material in the z-direction can also be observed. Moreover, the size of the stimulation material in various relative locations of the signal element can also be determined on the computer screen using software (SEMICAPS Genie v. 1.0 desktop imaging system manufactured by SEMICAPS, Inc., Santa Clara, Calif.) in conjunction with the scanning electron micrograph.

Thickness Test

Figure 11:
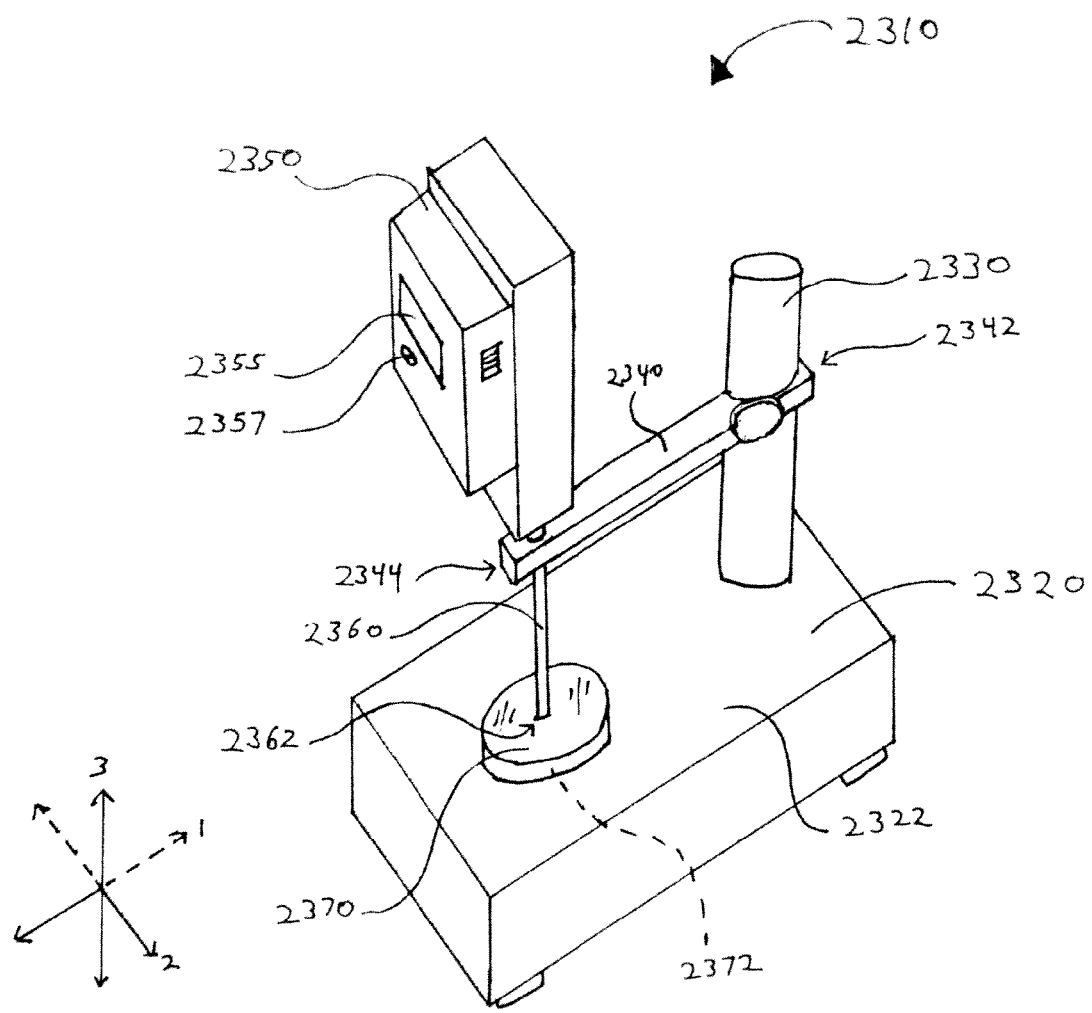
FIG. 11 is a perspective view of a thickness tester utilized in the Thickness Test.

The thickness value of a selected portion or section of an article is determined using a thickness tester such as seen in FIG. 11. The thickness tester 2310 includes a granite base 2320 having a clamp shaft 2330 where the top surface 2322 of the granite base 2320 is flat and smooth. A suitable granite base is a Starret Granite Base, model 653G (available from The L.S. Starrett Company, having a place of business located in Athol, Mass., U.S.A.) or equivalent. A clamp arm 2340 is secured to the clamp shaft 2330 at one end 2342 of the clamp arm 2340, and a digital indicator 2350 is secured to the clamp arm 2340 at the opposing end 2344. A suitable indicator is a Mitutoyo ID-H Series 543 Digimatic Indicator (available from Mitutoyo America Corp., having a place of business located in Aurora, Ill., U.S.A.) or equivalent. Extending downward from the indicator 2350 is a vertically-movable plunger 2360. Attached to the distal end 2362 of the plunger 2360 is a circular platen 2370 having a diameter of 76.2 mm. The platen 2370 is constructed of acrylic and is flat and smooth on at least the bottom surface 2372. The thickness and weight of the platen 2370 is configured such that the thickness tester 2310 provides a pressure of 0.345 kPa (0.05 psi).

To perform the procedure, a sample of the specimen to be tested is cut to a size having dimensions of at least 90 mm by 102 mm. The platen 2370 and plunger 2360 unit is gently lowered such that the bottom surface 2372 is in direct contact with the top surface 2322 of the granite base 2320, and the digital indicator 2350 is then tared (i.e., zeroed) by pressing the "zero" button 2357. The digital display 2355 of the digital indicator 2350 should display "0.00 mm" or equivalent. The platen 2370 and plunger 2360 unit is then raised and the sample is placed onto the top surface 2322 of the granite base 2320 such that the sample is centered under the platen 2370. The platen 2370 and plunger 2360 unit is then gently lowered onto the sample to provide a pressure of 0.345 kPa (0.05 psi).

After 3 seconds, the measurement from the digital display 2355 is recorded to the nearest 0.01 mm.

Aqueous Insult Procedure

Figure 9A:
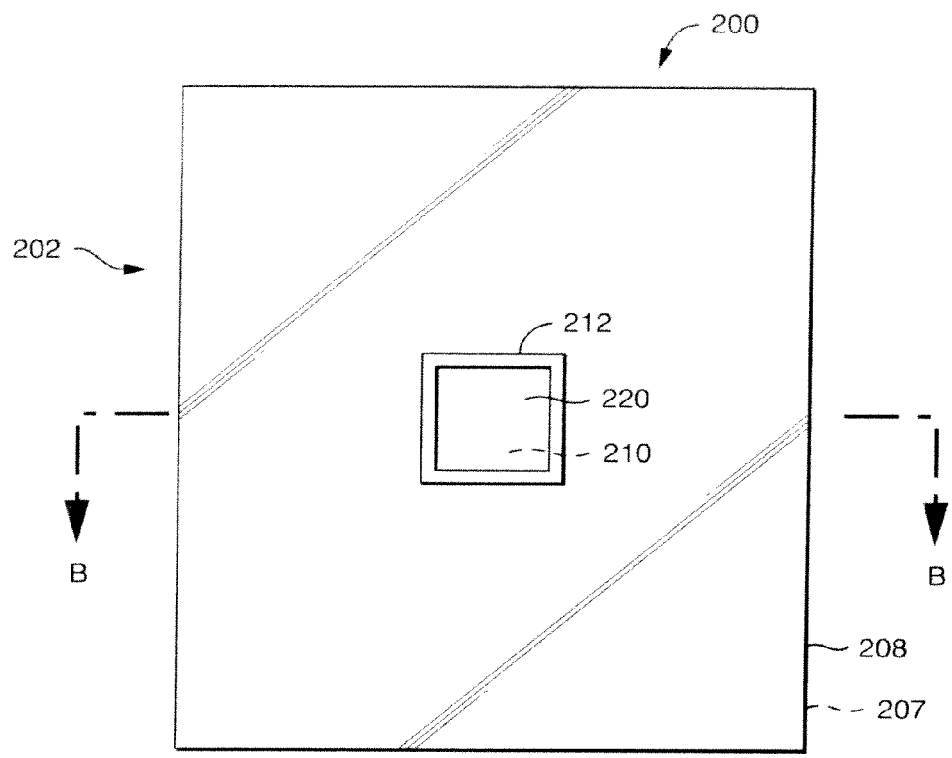
FIG. 9A is a top view of the test equipment for the Aqueous Insult Procedure.
Figure 9B:
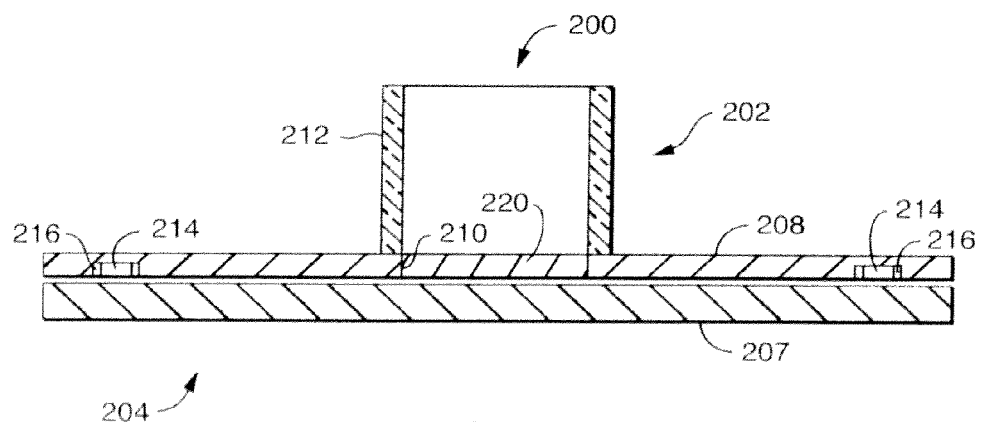
FIG. 9B is a cross-section of the test equipment of FIG. 9A taken at line B-B.

The Aqueous Insult Procedure provides a suitable method for simulating a single aqueous insult, or multiple aqueous insults, of a sample. A suitable apparatus for performing the Aqueous Insult Procedure is shown in FIGS. 9A and 9B and is generally indicated at 200. The test apparatus 200 comprises upper and lower assemblies, generally indicated at 202 and 204 respectively, wherein the lower assembly 204 comprises a generally 18 cm×18 cm square lower plate 207 constructed of a transparent PLEXIGLAS (available from Degussa AG, a business having offices located in Dusseldorf, Germany) for supporting the sample during the test.

The upper assembly 202 comprises a generally 18 cm×18 cm square upper plate 208 constructed of the same transparent PLEXIGLAS as lower plate 207 and having a 4 cm×4 cm square central opening 210 formed therein. A 4 cm×4 cm square (inner dimensions) fluid delivery tube 212 constructed of the same transparent PLEXIGLAS as lower plate 207 is secured to the upper plate 208 at the central opening 210 and extends upward substantially perpendicular to the upper plate. Accordingly, the central opening 210 of the upper plate 208 should have equal dimensions to the inner dimensions of the delivery tube 212 and should be aligned where the delivery tube 212 is mounted on top of the upper plate 208.

Pin elements 214 are located near the outside corners of the lower plate 207, and corresponding recesses 216 in the upper plate 208 are sized to receive the pin elements 214 to properly align and position the upper assembly 202 onto the lower assembly 204 during testing. The weight of the upper assembly 202 (including the upper plate 208 and delivery tube 212) is approximately 360 grams.

To run the Aqueous Insult Procedure, the sample to be tested is cut to have dimensions of 40 mm×40 mm to form a test sample 220. With the upper assembly 202 attached to the lower assembly 204, the test sample 220 is placed into the delivery tube 212 and fitted into the central opening 210 of the upper plate 208 so that substantially the entire bottom-side of the test sample 220 is in direct contact with the lower plate 207. Once the test sample 220 is in place, 20 grams of tap water at 23° C. (i.e. a first aqueous insult) is poured into the top of the delivery tube 212 and allowed to flow down into the sample 220. A stopwatch is started when the first drop of water contacts the sample 220. After 10 seconds, without stopping the stopwatch, the upper assembly is quickly removed and any excess water remaining on the sample is removed by tilting the lower plate 207, being careful that the test sample 220 does not move. Particular properties of the test samples can then be measured at particular time intervals, as desired. After 4.5 minutes (i.e., 30 seconds prior to the next insult), the upper assembly 202 is re-attached to the lower assembly 204 via the pins 214 with the test sample 220 being substantially centered within the opening 210. At 5 minutes on the stopwatch, another 20 grams of tap water at 23° C. (i.e. a second aqueous insult) is poured into the top of the delivery tube 212 and allowed to flow down into the sample 220. 10 seconds after the first drop of water contacts the test sample 220, the upper assembly is quickly removed again and any excess water remaining on the sample is removed by tilting the lower plate 207, being careful that any undissolved test sample 220 does not move. Particular properties of the test sample can again be measured at particular time intervals, as desired. The procedure is repeated for a third, fourth and subsequent insults until either the sample has completely dissolved, or until the stimulation effect has ceased.

DEFINITIONS

It should be noted that, when employed in the present disclosure, the terms "comprises," "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "absorbent article" generally refers to devices which can absorb and contain fluids. For example, personal care absorbent articles refer to devices which are placed against or near the skin to absorb and contain the various fluids discharged from the body.

The term "attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements.

The term "bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements.

The term "coform" refers to a blend of meltblown fibers and absorbent fibers such as cellulosic fibers that can be formed by air forming a meltblown polymer material while simultaneously blowing air-suspended fibers into the stream of meltblown fibers. The coform material may also include other materials, such as superabsorbent materials. The meltblown fibers and absorbent fibers are collected on a forming surface, such as provided by a foraminous belt. The forming surface may include a gas-pervious material that has been placed onto the forming surface. Exemplary coform processes are described in U.S. Pat. No. 4,100,324 to Anderson et al.; U.S. Pat. No. 4,587,154 to Hotchkiss et al.; U.S. Pat. No. 4,604,313 to McFarland et al.; U.S. Pat. No. 4,655,757 to McFarland et al.; U.S. Pat. No. 4,724,114 to McFarland et al.; U.S. Pat. No. 4,100,324 to Anderson et al.; and U.K. Patent GB 2,151,272 to Minto et al., each of which is incorporated herein by reference in a manner that is consistent herewith.

The term "complex liquid" describes a liquid generally characterized as being a viscoelastic liquid pertaining primarily to aqueous liquids associated with menstruation.

The term "connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements.

The term "disposable" is used herein to describe absorbent articles that are not intended to be laundered or otherwise restored or reused as an absorbent article after a single use.

The terms "disposed on," "disposed along," "disposed with," or "disposed toward" and variations thereof are intended to mean that one element can be integral with another element, or that one element can be a separate structure bonded to or placed with or placed near another element.

The terms "elastic," "elasticized," "elasticity," and "elastomeric" and derivatives thereof mean that property of a material or composite by virtue of which it tends to recover its original size and shape after removal of a force causing a deformation. Suitably, an elastic material or composite can be elongated by at least 50 percent of its relaxed length and will recover, upon release of the applied force, at least 40 percent of its elongation.

The term "extensible" refers to a material or composite which is capable of extension or deformation without breaking, but does not substantially recover its original size and shape after removal of a force causing the extension or deformation (i.e., less than 40 percent recovery). Suitably, an extensible material or composite can be elongated by at least 50 percent of its relaxed length.

The term "fiber" refers to a continuous or discontinuous member having a high ratio of length to diameter or width. Thus, a fiber may be a filament, a thread, a strand, a yarn, or any other member or combination of these members.

The term "health/medical absorbent articles" includes a variety of professional and consumer health-care products including, but not limited to, products for applying hot or cold therapy, medical gowns (i.e., protective and/or surgical gowns), surgical drapes, caps, gloves, face masks, bandages, wound dressings, wipes, covers, containers, filters, disposable garments and bed pads, medical absorbent garments, underpads, and the like.

The term "household/industrial absorbent articles" includes construction and packaging supplies, products for cleaning and disinfecting, wipes, covers, filters, towels, disposable cutting sheets, bath tissue, facial tissue, nonwoven roll goods, home-comfort products including pillows, pads, mats, cushions, masks and body care products such as products used to cleanse or treat the skin, laboratory coats, coveralls, trash bags, pet care absorbent liners, laundry soil/ink absorbers, and the like.

The term "hydrophilic" describes materials which are wetted by aqueous liquids in contact with the materials. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, materials having contact angles less than 90 degrees are designated "wettable" or hydrophilic, and fibers having contact angles greater than 90 degrees are designated "nonwettable" or "hydrophobic".

The term "join" and its derivatives refer to the connecting, adhering, bonding, attaching, sewing together, or the like, of two elements. Two elements will be considered to be joined together when they are integral with one another or joined directly to one another or indirectly to one another, such as when each is directly joined to intermediate elements.

The term "liquid impermeable," when used in describing a layer or multi-layer laminate, means that liquid, such as urine, menses or bowel movement, will not pass through the layer or laminate, under ordinary use conditions, in a direction generally perpendicular to the plane of the layer or laminate at the point of liquid contact.

The term "liquid permeable" refers to any material that is not liquid impermeable.

The term "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. In the particular case of a coform process, the meltblown fiber stream intersects with one or more material streams that are introduced from a different direction. Thereafter, the meltblown fibers and other optional materials are carried by the high velocity gas stream and are deposited on a collecting surface. The distribution and orientation of the meltblown fibers within the formed web is dependent on the geometry and process conditions. Exemplary meltblown processes are described in various patents and publications, including NRL Report 4364, "Manufacture of Super-Fine Organic Fibers" by V. A. Wendt, E. L. Boone and C. D. Fluharty; NRL Report 5265, "An Improved Device For the Formation of Super-Fine Thermoplastic Fibers" by K. D. Lawrence, R. T. Lukas and J. A. Young; and U.S. Pat. No. 3,849,241 to Butin et al. and U.S. Pat. No. 5,350,624 to Georger et al., each of which is incorporated herein by reference in a manner that is consistent herewith.

The terms "nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblown processes, spunbond processes, air laying processes, and bonded-carded-web processes.

The term "personal care absorbent articles" includes, but is not limited to, absorbent articles such as diapers, diaper pants, baby wipes, training pants, absorbent underpants, child care pants, swimwear, and other disposable garments; feminine care products including sanitary napkins, wipes, menstrual pads, menstrual pants, panty liners, panty shields, interlabials, tampons, and tampon applicators; adult-care products including wipes, pads such as breast pads, containers, incontinence products, and urinary shields; clothing components; bibs; athletic and recreation products; and the like.

The term "sports/construction absorbent articles" includes headbands, wrist bands and other aids for absorption of perspiration, absorptive windings for grips and handles of sports equipment, and towels or absorbent wipes for cleaning and drying off equipment during use.

The terms "spunbond" and "spunbonded fiber" refer to fibers which are formed by extruding filaments of molten thermoplastic material from a plurality of fine, usually circular, capillaries of a spinneret, and then rapidly reducing the diameter of the extruded filaments.

The term "stretchable" means that a material can be stretched, without breaking, by at least 50 percent in at least one direction.

The term "superabsorbent material" refers to a water-swellable, water-insoluble organic or inorganic material capable, under the most favorable conditions, of absorbing at least about ten times its weight and, more desirably, at least about thirty times its weight in an aqueous solution containing about 0.9 weight percent sodium chloride.

The term "target zone" refers to an area of an absorbent article where it is particularly desirable for the majority of a fluid insult, such as urine, menses, or bowel movement, to initially contact. In particular, for an absorbent article of the present invention, the insult target zone refers to the area of the absorbent core extending a distance equal to 15% of the total length and width of the article from the insult point in all directions.

The term "thermoplastic" describes a material that softens when exposed to heat and which substantially returns to a non-softened condition when cooled to room temperature.

The term "% by weight," "weight %," "wt %" or derivative therof, when used herein, is to be interpreted as based on the dry weight, unless otherwise specified.

These terms may be defined with additional language in the remaining portions of the specification.

DETAILED DESCRIPTION

The improved signal element member (hereinafter referred to as a "signal element") of this invention is useful in absorbent articles. An absorbent article of the present invention generally can have an absorbent core, and can optionally include a topsheet and/or a backsheet, where the absorbent core can be disposed between the topsheet and the backsheet. The signal element comprises a stimulation material and a water-soluble polymeric buffering film.

Figure 2:
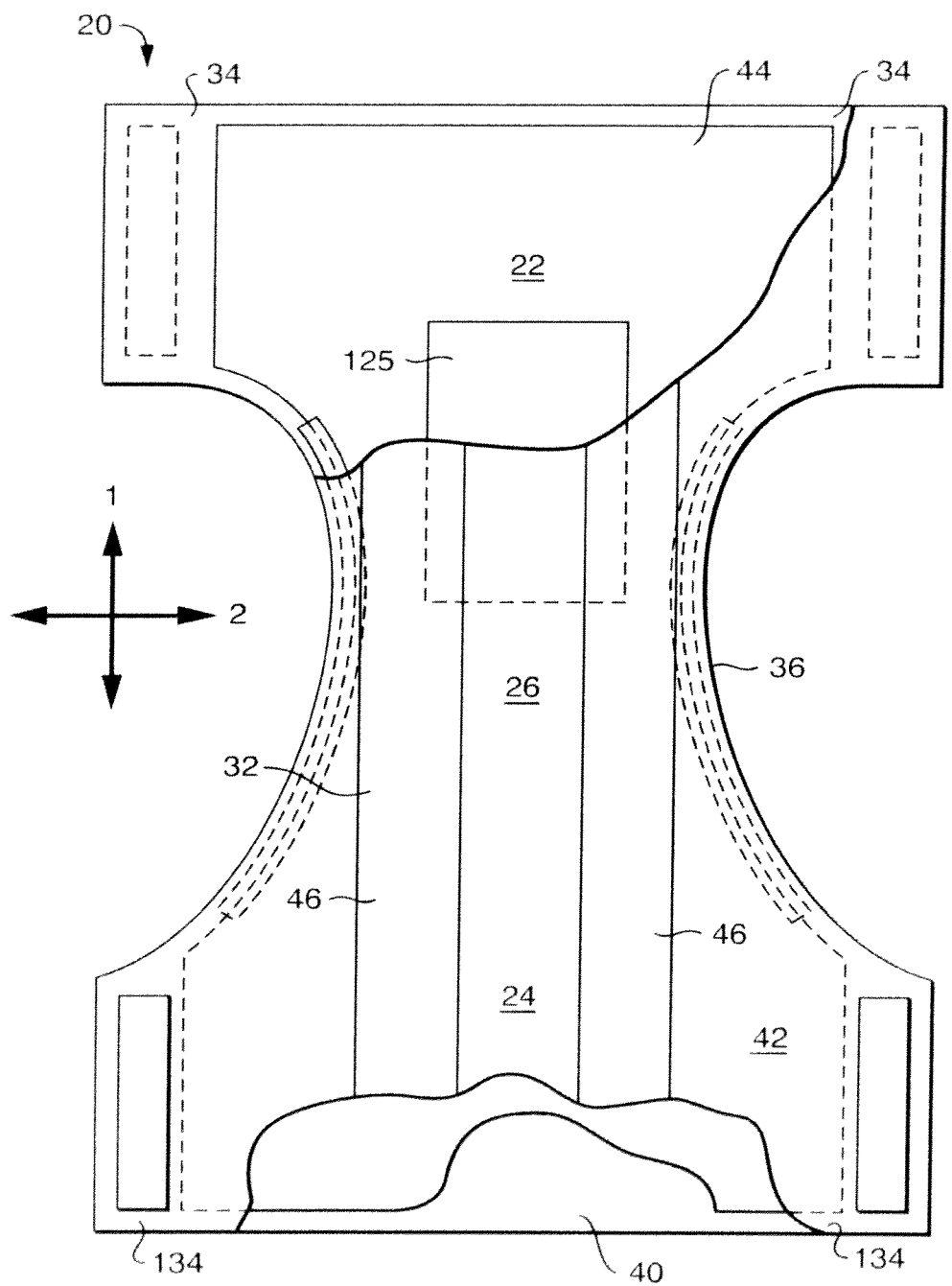

To gain a better understanding of the present invention, attention is directed to FIG. 1 and FIG. 2 for exemplary purposes showing a training pant of the present invention. It is understood that the present invention is suitable for use with various other absorbent articles, including but not limited to other personal care absorbent articles, health/medical absorbent articles, household/industrial absorbent articles, sports/construction absorbent articles, and the like, without departing from the scope of the present invention.

Various materials and methods for constructing training pants are disclosed in U.S. Pat. No. 6,761,711 to Fletcher et al.; U.S. Pat. No. 4,940,464 to Van Gompel et al.; U.S. Pat. No. 5,766,389 to Brandon et al., and U.S. Pat. No. 6,645,190 to Olson et al., each of which is incorporated herein by reference in a manner that is consistent herewith.

FIG. 1 illustrates a training pant 20 in a partially fastened condition, and FIG. 2 illustrates a training pant 20 in an opened and unfolded state. The training pant 20 defines a longitudinal direction 1 that extends from the front of the training pant when worn to the back of the training pant. Perpendicular to the longitudinal direction 1 is a lateral direction 2.

The training pant 20 defines a front region 22, a back region 24, and a crotch region 26 extending longitudinally between and interconnecting the front and back regions 22, 24. The pant also defines an inner surface (i.e., body-facing surface) adapted in use (e.g., positioned relative to the other components of the pant) to be disposed toward the wearer, and an outer surface (i.e., garment-facing surface) opposite the inner surface. The training pant has a pair of laterally opposite side edges and a pair of longitudinally opposite waist edges.

The illustrated pant 20 may include a chassis 32, a pair of laterally opposite front side panels 34 extending laterally outward at the front region 22 and a pair of laterally opposite back side panels 134 extending laterally outward at the back region 24.

The chassis 32 includes a backsheet 40 and a topsheet 42 that may be joined to the backsheet 40 in a superimposed relation therewith by adhesives, ultrasonic bonds, thermal bonds or other conventional techniques. The chassis 32 may further include an absorbent core 44 such as shown in FIG. 2 disposed between the backsheet 40 and the topsheet 42 for absorbing fluid body exudates exuded by the wearer, and may further include a pair of containment flaps 46 secured to the topsheet 42 or the absorbent core 44 for inhibiting the lateral flow of body exudates.

The backsheet 40, the topsheet 42 and the absorbent core 44 may be made from many different materials known to those skilled in the art. All three layers, for instance, may be extensible and/or elastically extensible. Further, the stretch properties of each layer may vary in order to control the overall stretch properties of the product.

The backsheet 40, for instance, may be breathable and/or may be fluid impermeable. The backsheet 40 may be constructed of a single layer, multiple layers, laminates, spunbond fabrics, films, meltblown fabrics, elastic netting, microporous webs or bonded-carded-webs. The backsheet 40, for instance, can be a single layer of a fluid impermeable material, or alternatively can be a multi-layered laminate structure in which at least one of the layers is fluid impermeable.

The backsheet 40 can be biaxially extensible and optionally biaxially elastic. Elastic non-woven laminate webs that can be used as the backsheet 40 include a non-woven material joined to one or more gatherable non-woven webs or films. Stretch bonded laminates (SBL) and neck bonded laminates (NBL) are examples of elastomeric composites.

Examples of suitable nonwoven materials are spunbond-meltblown fabrics, spunbond-meltblown-spunbond fabrics, spunbond fabrics, or laminates of such fabrics with films, or other nonwoven webs. Elastomeric materials may include cast or blown films, meltblown fabrics or spunbond fabrics composed of polyethylene, polypropylene, or polyolefin elastomers, as well as combinations thereof. The elastomeric materials may include PEBAX elastomer (available from AtoFina Chemicals, Inc., a business having offices located in Philadelphia, Pa. U.S.A.), HYTREL elastomeric polyester (available from Invista, a business having offices located in Wichita, Kans. U.S.A.), KRATON elastomer (available from Kraton Polymers, a business having offices located in Houston, Tex., U.S.A.), or strands of LYCRA elastomer (available from Invista), or the like, as well as combinations thereof. The backsheet 40 may include materials that have elastomeric properties through a mechanical process, printing process, heating process or chemical treatment. For example, such materials may be apertured, creped, neck-stretched, heat activated, embossed, and micro-strained, and may be in the form of films, webs, and laminates.

One example of a suitable material for a biaxially stretchable backsheet 40 is a breathable elastic film/nonwoven laminate, such as described in U.S. Pat. No. 5,883,028, to Morman et al., incorporated herein by reference in a manner that is consistent herewith. Examples of materials having two-way stretchability and retractability are disclosed in U.S. Pat. No. 5,116,662 to Morman and U.S. Pat. No. 5,114,781 to Morman, each of which is incorporated herein by reference in a manner that is consistent herewith. These two patents describe composite elastic materials capable of stretching in at least two directions. The materials have at least one elastic sheet and at least one necked material, or reversibly necked material, joined to the elastic sheet at least at three locations arranged in a nonlinear configuration, so that the necked, or reversibly necked, web is gathered between at least two of those locations.

The topsheet 42 is suitably compliant, soft-feeling and non-irritating to the wearer's skin. The topsheet 42 is also sufficiently liquid permeable to permit liquid body exudates to readily penetrate through its thickness to the absorbent core 44. A suitable topsheet 42 may be manufactured from a wide selection of web materials, such as porous foams, reticulated foams, apertured plastic films, woven and non-woven webs, or a combination of any such materials. For example, the topsheet 42 may include a meltblown web, a spunbonded web, or a bonded-carded-web composed of natural fibers, synthetic fibers or combinations thereof. The topsheet 42 may be composed of a substantially hydrophobic material, and the hydrophobic material may optionally be treated with a surfactant or otherwise processed to impart a desired level of wettability and hydrophilicity.

The topsheet 42 may also be extensible and/or elastomerically extensible. Suitable elastomeric materials for construction of the topsheet 42 can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon, a business having offices located in Cleveland, Ohio U.S.A.), or PEBAX elastomers. The topsheet 42 can also be made from extensible materials such as those described in U.S. Pat. No. 6,552,245 to Roessler et al. which is incorporated herein by reference in a manner that is consistent herewith. The topsheet 42 can also be made from biaxially stretchable materials as described in U.S. Pat. No. 6,969,378 to Vukos et al. which is incorporated herein by reference in a manner that is consistent herewith.

The article 20 can optionally further include a surge management layer which may be located adjacent the absorbent core 44 and attached to various components in the article 20 such as the absorbent core 44 or the topsheet 42 by methods known in the art, such as by using an adhesive. In general, a surge management layer helps to quickly acquire and diffuse surges or gushes of liquid that may be rapidly introduced into the absorbent structure of the article. The surge management layer can temporarily store the liquid prior to releasing it into the storage or retention portions of the absorbent core 44. Examples of suitable surge management layers are described in U.S. Pat. No. 5,486,166 to Bishop et al.; U.S. Pat. No. 5,490,846 to Ellis et al.; and U.S. Pat No. 5,820,973 to Dodge et al., each of which is incorporated herein by reference in a manner that is consistent herewith.

The article 20 can further comprise an absorbent core 44. The absorbent core 44 may have any of a number of shapes. For example, it may have a 2-dimensional or 3-dimensional configuration, and may be rectangular shaped, triangular shaped, oval shaped, race-track shaped, I-shaped, generally hourglass shaped, T-shaped and the like. It is often suitable for the absorbent core 44 to be narrower in the crotch portion 26 than in the rear 24 or front 22 portion(s). The absorbent core 44 can be attached in an absorbent article 20, such as to the backsheet 40 and/or the topsheet 42 for example, by bonding means known in the art, such as ultrasonic, pressure, adhesive, aperturing, heat, sewing thread or strand, autogenous or self-adhering, hook-and-loop, or any combination thereof.

The absorbent core 44 can be formed using methods known in the art. While not being limited to the specific method of manufacture, the absorbent core 44 can utilize forming drum systems, for example, see U.S. Pat. No. 4,666,647 to Enloe et al., U.S. Pat. No. 4,761,258 to Enloe, U.S. Pat. No. 6,630,088 to Venturino et al., and U.S. Pat. No. 6,330,735 to Hahn et al., each of which is incorporated herein by reference in a manner that is consistent herewith. Examples of techniques which can introduce a selected quantity of optional superabsorbent particles into a forming chamber are described in U.S. Pat. No. 4,927,582 to Bryson and U.S. Pat. No. 6,416,697 to Venturino et al., each of which is incorporated herein by reference in a manner that is consistent herewith.

In some desirable aspects, the absorbent core 44 includes cellulose fiber and/or synthetic fiber, such as meltblown fiber, for example. Thus, in some aspects, a meltblown process can be utilized, such as to form the absorbent core 44 in a coform line. In some aspects, the absorbent core 44 can have a significant amount of stretchability. For example, the absorbent core 44 can comprise a matrix of fibers which includes an operative amount of elastomeric polymer fibers. Other methods known in the art can include attaching superabsorbent polymer particles to a stretchable film, utilizing a nonwoven substrate having cuts or slits in its structure, and the like.

The absorbent core 44 can additionally or alternatively include absorbent and/or superabsorbent material. Accordingly, the absorbent core 44 can comprise a quantity of superabsorbent material and optionally fluff contained within a matrix of fibers. In some aspects, the total amount of superabsorbent material in the absorbent core 44 can be at least about 10% by weight of the core, such as at least about 30%, or at least about 60% by weight or at least about 90%, or between about 10% and about 98% by weight of the core, or between about 30% to about 90% by weight of the core to provide improved benefits. Optionally, the amount of superabsorbent material can be at least about 95% by weight of the core, such as up to 100% by weight of the core. In other aspects, the amount of absorbent fiber of the present invention in the absorbent core 44 can be at least about 5% by weight of the core, such as at least about 30%, or at least about 50% by weight of the core, or between about 5% and 90%, such as between about 10% and 70% or between 10% and 50% by weight of the core. In still other aspects, the absorbent core 44 can optionally comprise about 35% or less by weight unmodified fluff, such as about 20% or less, or 10% or less by weight unmodified fluff.

It should be understood that the absorbent core 44 is not restricted to use with superabsorbent material and optionally fluff. In some aspects, the absorbent core 44 may additionally include materials such as surfactants, ion exchange resin particles, moisturizers, emollients, perfumes, fluid modifiers, odor control additives, and the like, and combinations thereof. In addition, the absorbent core 44 can include a foam.

Figure 3:
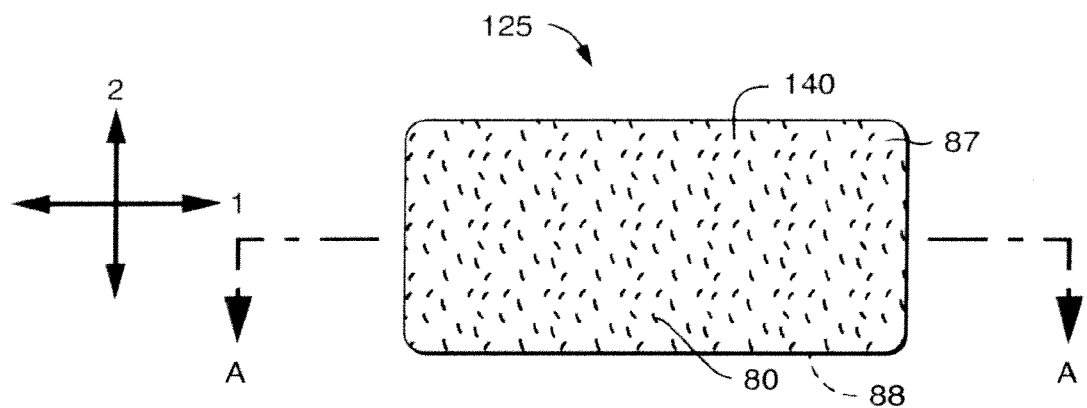
FIG. 3 is top view of a signal element of the present invention having a uniform distribution of stimulation material.

The absorbent article of the present invention also includes a signal element 125 that is positioned and adapted to create a distinct physical sensation as the article 20 is insulted with an aqueous liquid. The signal element 125 can have a longitudinal-direction 1 and a transverse-direction 2, which together can form a plane when in a laid-flat condition, hereinafter referred to as the "x-y plane." As seen in FIG. 3, the signal element 125 can define a signal element body-facing surface 87 intended to be disposed toward the wearer in use (i.e., an inner surface) and a signal element garment-facing surface 88 intended to be disposed away from the wearer in use, opposite the member inner surface (i.e., an outer surface).

The signal element 125 can have any desired shape. For example, it may have a 2-dimensional or 3-dimensional configuration, and may be rectangular shaped, triangular shaped, circular-shaped, oval shaped, race-track shaped, I-shaped, generally hourglass shaped, T-shaped and the like. In some aspects, the signal element 125 can have no particular defined shape, but rather can have a random shape. Thus, the dimensions in the x-y plane can vary as desired. The signal element 125 can also have a thickness dimension in the z-direction as desired. By way of example only, a suitable thickness of the signal element 125 can be between 0.1 mm and 10 mm, such as between 0.2 mm and 5 mm or between 0.5 mm and 3 mm as measured by the Thickness Test. The signal element 125 can also have a desired stiffness or flexibility. In some desirable aspects, the signal element 125 will have approximately the same flexibility as the overall flexibility of the article.

Because the physical sensation resulting from the signal element 125 is noticeable to the wearer, the wearer's ability to recognize when a liquid insult has occurred (and/or is occurring) will be enhanced. The signal element 125 can be positioned within the article 20 in any operative location such that a user can detect a physical sensation as a result of the signal element 125 receiving an aqueous liquid insult. For example, in some aspects, the signal element 125 can be disposed as a separate layer adjacent to the body-facing surface of an absorbent core 44. In other aspects, the signal element 125 can be disposed as a separate layer adjacent the garment-facing surface and/or the body-facing surface of a topsheet 42. In still other exemplary aspects, the signal element 125 can be disposed as a separate layer adjacent to the body-facing surface or garment-facing surface of a surge layer, for example. Other configurations are also suitable for the invention as would be readily apparent to those skilled in the art.

The signal element 125 of the present invention comprises a stimulation material 80 and a water-soluble polymeric buffering film 140. The purpose of the stimulation material 80 is to provide the user with a perceptible sensation when a fluid insult is occurring and/or has occurred. The stimulation material 80 is preferably in the form of a solid. As used in this context, the term "solid" as it refers to stimulation materials can include particles, flakes, fibers, agglomerates, granules, powders, spheres, pulverized materials, tablets or the like, as well as combinations thereof. The solids can have any desired shape such as, for example, cubic, rod-like, polyhedral, spherical or semi-spherical, rounded or semi-rounded, angular, irregular, and the like. Stimulation materials 80 for use in the disposable absorbent article 20 include those that dissolve in an aqueous liquid. The solubility of such stimulation materials 80 is desirably from 0.1 to 6 grams of material per gram of water (g/g), such as from about 0.1 to about 3 g/g.

As can be appreciated, the signal element 125 of the present invention can define a total amount of stimulation material 80, by weight. For example, in one aspect, the signal element 125 can include 0.5 to 30 grams of stimulation material 80, such as 1 to 20 grams of stimulation material 80, or 1 to 10 grams of stimulation material 80.

Figure 4:
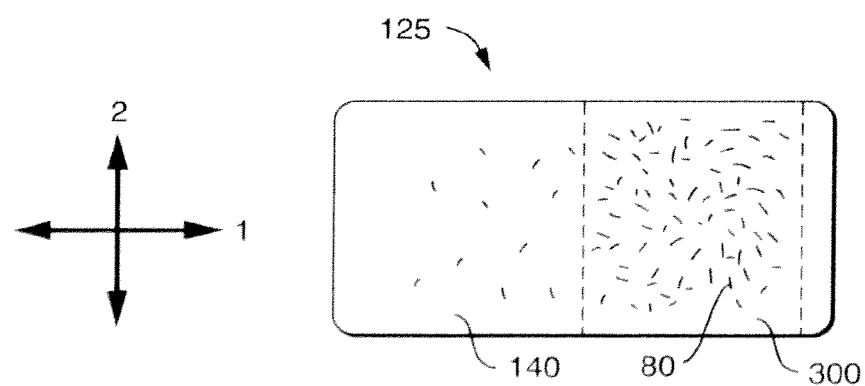
FIG. 4 is a top view of a signal element of the present invention having a nonuniform distribution of stimulation material.

The stimulation material 80 can be disposed within the signal element 125 in a variety of configurations. For example, as seen in FIG. 3, the stimulation material 80 can be distributed in a substantially uniform manner in the x-y plane, such that all areas or regions of the signal element 125 have substantially equal amounts of stimulation material 80, measured by weight. In other examples, the stimulation material 80 can be suitably disposed within the signal element 125 in a nonuniform distribution in the x-y plane, measured by weight. In such an aspect, such as seen in FIG. 4, the stimulation material 80 can be strategically located within the signal element 125 to maximize the effectiveness of the article 20 in use, such as in a target zone 300 as determined with respect to the absorbent article 20, as defined above. Other nonuniform distributions in the x-y plane are also suitable for the invention as would be readily apparent to those skilled in the art.

Figure 5:
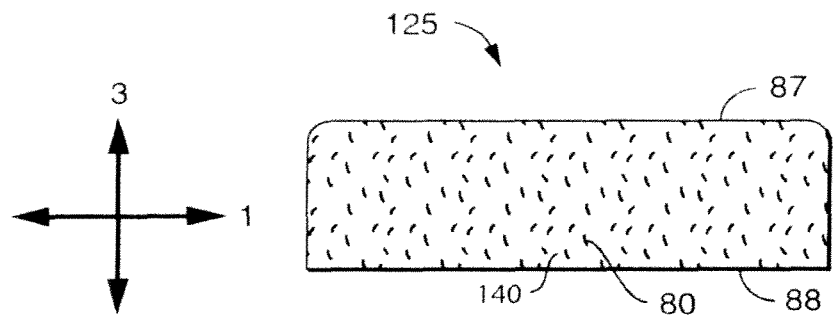
FIG. 5 is a longitudinal cross-section view of the signal element of FIG. 3 taken along line A-A having a uniform distribution of stimulation material.
Figure 6:
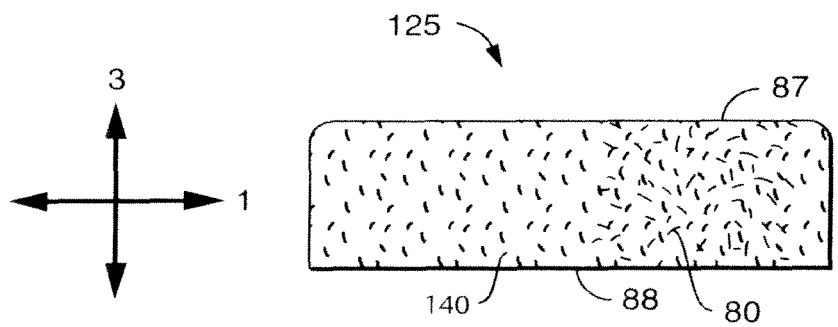
FIG. 6 is a longitudinal cross-section view of a signal element of the present invention having a non-uniform distribution of stimulation material.
Figure 7:
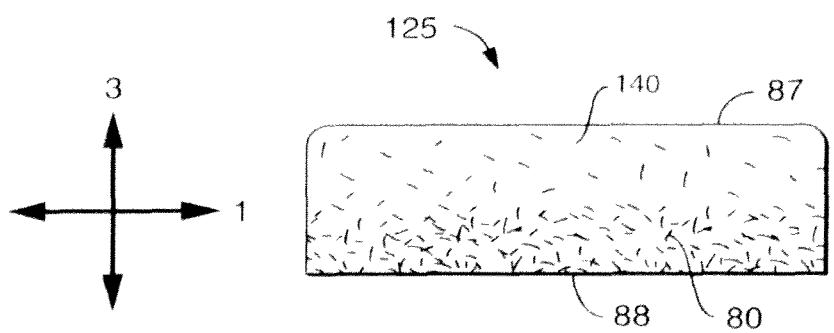
FIG. 7 is a longitudinal cross-section view of a signal element of the present invention having a non-uniform distribution of stimulation material.

In some aspects, such as seen in FIG. 5, the stimulation material 80 can be distributed within the signal element 125 in a uniform distribution in the z-direction 3, as measured by weight. In some aspects, the stimulation material 80 can be distributed within the signal element 125 in a nonuniform distribution in the z-direction 3, as measured by weight. In such an arrangement, stimulation material 80 can be disposed within the signal element 125 in greater or lesser amounts (measured by weight) in some regions of the signal element 125 as compared to other regions of the signal element 125. For example, such as seen in FIGS. 6 and 7, the distribution of stimulation material 80 can be suitably nonuniform through the longitudinal cross-section. In some aspects, the distribution of simulation material 80 can additionally or alternatively be nonuniform in the transverse cross-section. Other nonuniform distributions in the z-direction 3 are also suitable for the invention as would be well-known to those skilled in the art. One suitable method for determining the distribution of the stimulation material 80 within the signal element 125 is the Particle Distribution Test.

In some aspects, the stimulation material 80 can define a particle size distribution within the signal element 125. For example, the particle size distribution can be from a smaller stimulation material particle size to a larger stimulation material particle size measured from the body-facing surface 87 to the garment-facing surface 88 of the signal element 125. As such, the signal element 125 can include relatively larger sized stimulation material and can also include relatively smaller sized stimulation material. In some aspects, depending on the location of the relatively smaller stimulation material 80, the signal element 125 can present a relatively smooth, pleasing surface toward the wearer as relatively smaller materials may be closer to the body-facing surface 87. A suitable method for determining the particle size of the stimulation material 80 and the particle size distribution of the stimulation material 80 associated with the signal element 125 is by the Particle Size Test.

In some exemplary aspects, at least 10 wt % of the stimulation material 80 included in the signal element 125 can have a particle size of not greater than 200 microns. In other aspects, at least 10 wt % of the stimulation material 80 can have a particle size of greater than 500 microns. In yet other aspects, at least 25 wt % of the stimulation material 80 included in the signal element 125 can have a particle size of not greater than 200 microns. In still other aspects, at least 25 wt % of the stimulation material 80 can have a particle size of greater than 500 microns. Alternatively, at least 10 wt % of the stimulation material 80 included in the signal element 125 can have a particle size of not greater than 90 microns. In other aspects, at least 10 wt % of the stimulation material 80 can have a particle size of greater than 710 microns. In yet other aspects, at least 25 wt % of the stimulation material 80 included in the signal element 125 can have a particle size of not greater than 90 microns. In still other aspects, at least 25 wt % of the stimulation material 80 can have a particle size of greater than 710 microns.

In some aspects, at least 50 wt % of the stimulation material 80 can define a particle size of at least 500 microns. That is, if the signal element 125 contained a total amount of stimulation material 80 of 20 grams, at least 10 grams of that stimulation material 80 will have a particle size of at least 500 microns. In other aspects, at least 75 wt % of the stimulation material 80 can define a particle size of at least 500 microns. In another alternative, between 50 wt % and 85 wt % of the stimulation material 80 can define a particle size of at least 500 microns. In yet other aspects, at least 50 wt % of the stimulation material 80 can define a particle size of between 300 and 710 microns. In still other aspects, between 50 wt % and 85 wt % of the stimulation material 80 can define a particle size of between 300 and 710 microns. Accordingly, the signal element 125 can include suitably sized stimulation material 80 for improved benefits.

In some aspects, the stimulation material 80 having various particle sizes may be suitably disposed in certain portions of the signal element 125. In some particular aspects, at least 70 wt % of the stimulation material 80 in the 25-percent of the signal element 125 extending in the z-direction 3 adjacent the body-facing surface 87 can have a particle size of less than 300 microns. For example, if the signal element 125 is 10 mm thick in the z-direction 3, then at least 70 wt % of the stimulation material 80 in the 2.5 mm adjacent the body-facing surface 87 can have a particle size of less than 300 microns. In other aspects, the at least 70 wt % of the stimulation material 80 in the 25-percent of the signal element 125 extending in the z-direction 3 adjacent the inner surface 87 can have a particle size of less than 200 microns, such as less than 100 microns. In still other aspects, at least 70 wt % of the stimulation material 80 in the 25-percent of the signal element 125 extending in the z-direction 3 adjacent the body-facing surface 87 can have a particle size of between 200 microns and 500 microns.

A nonuniform distribution of the stimulation material 80 in the signal element 125 as described above can provide a number of benefits. For example, the signal element 80 can remain effective at providing a stimulating effect to the wearer in use while being less likely to cause irritation from a coarse surface due to stimulation material 80 being located proximate the wearer.

In some aspects, relatively larger stimulation material 80 can be disposed in certain portions of the signal element 125, such as disposed proximate the garment-facing surface 88. Alternatively, the relatively large stimulation material 80 can be disposed toward a z-directional centerline. As such, at least 70 wt % of the stimulation material 80 in the 25-percent of the signal element 125 extending in the z-direction 3 adjacent the garment-facing surface 88 of the signal element 125 can have a particle size of greater than 300 microns. In other aspects, at least 70 wt % of the stimulation material 80 in the 25-percent of the signal element 125 extending in the z-direction 3 adjacent the garment-facing surface 88 can have a particle size of greater than 500 microns, such as greater than 710 microns. In still other aspects, at least 70 wt % of the stimulation material 80 in the 25-percent of the signal element 125 extending in the z-direction 3 adjacent the garment-facing surface 88 can have a particle size of between 500 microns and 710 microns.

In some aspects, less than 10 wt % of the total amount of stimulation material 80 can be located in the 10-percent of the signal element 125 thickness extending in the z-direction 3 adjacent the body-facing surface 87. In other aspects, less than 10 wt % of the total amount of stimulation material 80 in the signal element 125 can be located in the 10-percent of the signal element thickness extending in the z-direction 3 adjacent the garment-facing surface 88. As such, in aspects where less than 10 wt % of the stimulation material 80 is adjacent the body-facing surface 87 and the garment-facing surface 88, assembly of the article 20 can be simplified because flipping of the signal element 125 during assembly of the article 20 may not negatively impact the performance of the article.

Figure 8A:
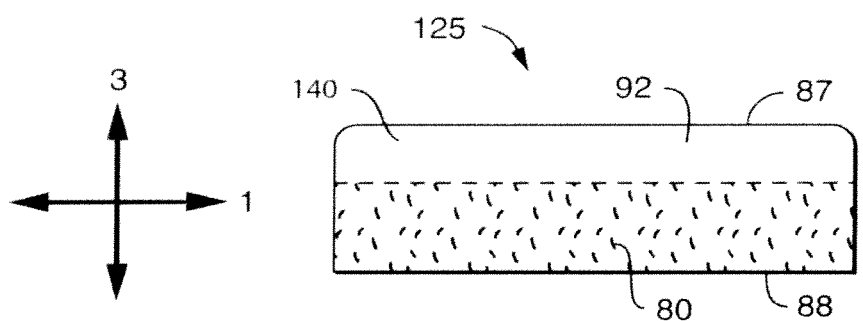
FIG. 8A is a longitudinal cross-section view of a signal element of the present invention having a first isolation zone.
Figure 8B:
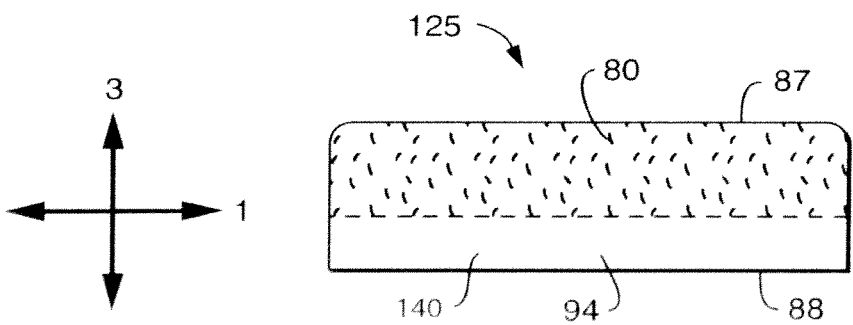
FIG. 8B is a longitudinal cross-section view of a signal element of the present invention having a second isolation zone.

With reference to FIG. 8A, in some aspects, at least 5%, such as at least 10%, or at least 25% of the signal element 125 adjacent the body-facing surface 87 as measured in the z-direction 3 can optionally be substantially free of stimulation material 80 to define a first isolation zone 92. In other aspects, between 10% and 25% of the signal element 125 adjacent the body-facing surface 87 as measured in the z-direction 3 can optionally be substantially free of stimulation material 80 to define a first isolation zone 92. In yet other aspects, such as seen in FIG. 8B, at least 5%, such as at least 10%, or at least 25% of the signal element 125 adjacent the garment-facing surface 88 as measured in the z-direction 3 can be free of stimulation material 80 to define a second isolation zone 94. In still other aspects, between 10% and 25% of the signal element 125 adjacent the garment-facing surface 88 can optionally be substantially free of stimulation material 80 to define a second isolation zone 94. Accordingly, the first isolation zone 92 and the second isolation zone 94 can be provided by a portion of the signal element 125 that is substantially free of stimulation material 80. As referenced above, a suitable method for determining the distribution of the stimulation material 80 within the signal element 125 is by the Particle Distribution Test. Accordingly, a magnified image of the z-directional cross-section of the signal element 125 can be taken. From the image, dimensions of isolation zones 92 and 94 may be measured.

In some aspects, the stimulation material 80 is responsive to contact with an aqueous solution such as urine, complex fluids or other aqueous body exudates to provide a stimulating effect, such as the absorption or release of heat, expulsion of a gas or application of pressure to the user, for example. In general, the mechanism by which this is accomplished is by dissolution of the stimulation material 80 in the aqueous solution, by swelling of the material 80 in the aqueous solution, or by reaction of the material 80 in the aqueous solution. For example, the stimulation material 80 may include particles that have a substantial energy difference between a dissolved state and a crystalline state so that energy in the form of heat is absorbed or released to the environment upon contact with urine, complex fluids or other aqueous body exudates, or the stimulation material 80 may release or absorb energy during swelling or reacting in the aqueous solution. The determination of the amount to be used and the location of the material 80 should be based in part on the desired stimulation effect.

In some aspects, the stimulation material 80 of the various aspects of the present invention can include a substance that provides a temperature change (referred to herein as a "temperature change agent") when placed near the wearer and contacted with an aqueous liquid. In some aspects, the temperature change can be an absorption or release of heat that is noticeable to the wearer. Absorption of heat by the temperature change agent (also referred to herein as a "cooling agent") will provide the wearer with a cool sensation, while a release of heat by the temperature change agent (also referred to herein as a "warming agent") will provide the wearer with a warm sensation. Reference is made to U.S. Patent Application Publication 2004/0254549 to Olson, et al., incorporated herein by reference in a manner that is consistent herewith, for additional information regarding the mechanism by which the temperature change sensation is accomplished. In some aspects, the cooling agents or warming agents can be provided in particulate form for ease of processing in the described embodiments.

To illustrate, in aspects where the stimulation material 80 is a temperature change agent, the body-facing surface 87 of the signal element 125 may suitably provide a temperature change (i.e., cooler or warmer) when insulted with an aqueous liquid of at least about 2° C., such as at least about 5° C., or at least about 10° C. Alternatively, the signal element 125 can provide a surface temperature change when insulted with an aqueous liquid of from 2° C. to 10° C., such as from 2° C. to 5° C.

In some aspects, the stimulation material 80 can include a temperature change agent in the form of a cooling agent, which can include those substances that absorb heat during dissolution from an insult. By way of example, polyols such as xylitol particles may be selected as cooling agents to provide a cooling sensation as xylitol particles absorb heat when dissolved in an aqueous liquid. Alternatively, other polyols such as sorbitol or erythritol may be advantageously selected to provide a cooling sensation. In yet other aspects, various combinations of the above stimulation materials 80 may be utilized. Suitable polyols can be obtained from Roquette America, Inc., a company having offices in Keokuk, Iowa, U.S.A., under the trade name of XYLIS ORB (xylitol) or NEOSORB (sorbitol). Such polyols can generally be obtained from the manufacturer in particular particle sizes, such as 90 microns, 300 microns, 500 microns, and the like for disposition in the signal element 125.

Other suitable stimulation materials 80 that absorb heat during dissolution include salt hydrates, such as sodium acetate ($H_2O$), sodium carbonate ($H_2O$), sodium sulfate ($H_2O$), sodium thiosulfate ($H_2O$), and sodium phosphate ($H_2O$); anhydrous salts such as ammonium nitrate, potassium nitrate, ammonium chloride, potassium chloride, and sodium nitrate; organic compounds such as urea and the like or combinations thereof.

In some aspects, the stimulation material 80 can include a temperature change agent in the form of a warming agent, which can include those substances that release heat during dissolution from an insult. Examples of materials that release heat during dissolution include manganese chloride, aluminum chloride, aluminum sulfate, potassium aluminum sulfate, and the like or combinations thereof. In some aspects, the warming agent can also include those substances that release heat during swelling. By way of illustration only, one suitable stimulation material 80 that releases heat during swelling is a lightly cross-linked partially neutralized polyacrylic acid.

The stimulation material 80 can also include ortho esters or ketals such as menthone ketals that result from reacting menthone with alcohols containing 1 to 8 carbons or polyols containing 2 to 8 carbons, and all structural and optical isomers thereof. Particular menthone ketals that may be suitable include menthone-glycerol ketal and menthone-propylene glycol ketal. Other suitable ketals are disclosed in U.S. Pat. No. 5,348,750 to Greenberg and U.S. Pat. No. 5,266,592 to Grub et al., which are incorporated herein by reference in a manner that is consistent herewith.

The selection of a particular temperature change agent and the determination of the amount to be used should be based in part on the desired temperature change. For example, in some aspects, the stimulation material 80 can be present in the signal element 125 at a basis weight of from about 20 to about 3000 grams/$m^2$ (gsm), such as about 50 gsm to about 2000 gsm, or about 100 gsm to about 1000 gsm. In some aspects, the disposable absorbent article 20 desirably provides a surface temperature change when wet of from about 2° C. to 15° C. To achieve this result, the temperature change substance, the amount used, and the location of the material should be selected so that the possible total energy change is from about 3 to about 30 calories per square centimeter (cal/$cm^2$), which may represent either a possible total energy release of from about 3 to about 30 cal/$cm^2$ or a possible total energy absorption of from about 3 to about 30 cal/$cm^2$, such as from about 6 to about 24 cal/$cm^2$, or about 12 to about 18 cal/$cm^2$.

By way of example only, urea particles may be selected to provide a cooling sensation. Urea has a heat of solution of approximately −60 calories per gram (cal/g). One exemplary add-on amount for the urea particles, for example, would be a basis weight of about 500 gsm to about 2000 gsm. The selection of urea particles at this basis weight range results in a possible total energy change of about 3 cal/$cm^2$ to about 24 cal/$cm^2$, such as about 3 cal/$cm^2$ to about 12 cal/$cm^2$, or about 3 cal/$cm^2$ to about 6 cal/$cm^2$.

Temperature change agents that absorb or release heat on contact with an aqueous solution desirably have a heat of solution, hydration, or reaction greater than about 30 cal/g, or less than about −30 cal/g. The heat of solution, hydration, or reaction is suitably within the range of from about 30 to about 90 cal/g or from about −30 to about −90 cal/g, such as from about 30 to about 70 cal/g or from about −30 to about −70 cal/g, such as xylitol at −32 cal/g or urea at −60 cal/g.

In some aspects, the stimulation material 80 is in the form of a pressure change agent. Such a material can result in a pressure change such as from an expandable element, or may be a foaming, fizzing, bubbling, gas release or other physical sensation such as where the user can feel a tingling sensation and/or hear a crackling sound, for example. Accordingly, the signal element 125 can include a stimulation material 80 in the form of a pressure change agent positioned within the article 20.

For example, the signal element 125 can be adapted to provide the wearer with an expanding or contracting dimensional change sensation. Dimensional change elements of this type are described in more detail in U.S. Pat. No. 5,649,914 to Glaug et al., which is incorporated herein by reference in a manner that is consistent herewith. A pressure change agent in the form of a dimensional change material includes materials that rapidly undergo a change in at least one dimension when exposed to an aqueous solution. The dimensional change is suitably either as an expansion to at least about 2 times a dry dimension or as a contraction to less than about one-half (½) of the dry dimension, such as a dimensional change of either an expansion to at least about 5 times the dry dimension or a contraction to less than about one-fifth (⅕) of the dry dimension. For example, the dimensional change material can have a wet height dimension that is at least about 5 times greater than its dry height dimension, such as at least about 10 times greater for improved performance. The height dimension of the dimensional change material is in the z-direction 3 of the signal element 125 so that the dimensional change is noticeable to the wearer of the absorbent article 20. In other aspects, the x-direction 1 and/or y-direction 2 of the signal element 125 can additionally or alternatively remain the same, expand, or contract when exposed to an aqueous solution. For example, in a particular aspect, the dimensional change material is capable of expanding to at least about 5 times its dry height in 10 seconds to at least about 10 times its dry height in 3 seconds for improved performance.

In some aspects, although not necessarily, the dimensional change agent can be generally hydrophobic so that the dimensional change material releases liquid to the absorbent article 20. For example, in one particular aspect, the dimensional change material can include a z-direction compressed cellulose sponge material having a dry height of about 0.9 mm and a wet height of about 9.5 mm The height dimension of this particular material is measured with the material under a compressive load of 0.2 psi (1.38 kPa). In this aspect, the noncompressed axes of the material, that is the x- and y-dimension directions, may expand less than about 10-percent from dry to wet states.

Suitable materials for use in the dimensional change material include expandable foams, compressed cellulose sponges, superabsorbents, or the like. Particularly, desirable expandable foams include those having open, large cell, reticulated structures. Examples of such expandable foams include O-CELL-O, available from General Mills, Inc., Tonawanda, N.Y., U.S.A., and those from Industrial Commercial Supply Co., Akron, Ohio, U.S.A. The material forming the dimensional change material may be softened by mechanical means or other suitable techniques so as to be less noticeable until urination occurs. One such means that is effective with compressed cellulose sponge is to run the material through a set of meshed gears with the gap between the gears set so that the material is sufficiently scored to make it pliable. In some aspects, the sponge materials are incorporated into the signal element 125 as relatively small pieces having desired dimensions.

In some aspects, the pressure change agent produces a gas, such as carbon dioxide. Gas generating materials of this type are described in more detail in U.S. Pat. No. 7,002,055 to Long et al., which is incorporated herein by reference in a manner that is consistent herewith. The gas produced upon wetting with urine, complex fluids or other body exudates can produce a sound, a smell, a tingling sensation or apply pressure to the user.

In some aspects, the signal element 125 can optionally include a surfactant. In some aspects, the gas producing materials can interact with the surfactant to produce a foam that applies pressure to the user. Thus, the surfactant component can be present as a foaming agent. For example, when a gas, such as carbon dioxide, is produced, the gas interacts with the surfactant and a bubble-filled foam is produced. These bubbles cause the article to swell and push against the skin of the wearer to alert the wearer of a liquid insult.

The surfactant used is not critical so long as it does not substantially irritate the skin upon contact, or adversely affect the efficacy of the stimulation material 80. A wide variety of surfactants may be suitable for use in accordance with the present invention. For example, suitable surfactants include anionic surfactants, nonionic surfactants, amphoteric surfactants, cationic surfactants, and combinations thereof. Examples of suitable anionic surfactants include alkyl benzene sulfonates, alkyl sulfates, alkyl ether sulfates, sulfosuccinates, and combinations thereof. Examples of suitable nonionic surfactants include ethoxylated alcohols, fatty acid alkanolamides, ethoxylated alkanolamides, amine oxides, and combinations thereof. Examples of suitable amphoteric surfactants include alkyl betaines, amidobetaines, and combinations thereof. Examples of suitable cationic surfactants include alkylammonium halides. In some aspects, the signal element 125 can include from about 0.1 grams to about 15 grams of surfactant.

In other aspects, a pressure change agent in the form of a gas producing material can include an aqueous-soluble effervescent solid material. Such aqueous-soluble effervescent solid material typically comprises pressurized gas-containing cells. When the solid material having pressurized gas-containing cells is contacted with urine or other body exudates, the solid material begins to dissolve and the pressurized gas is released from the cells during dissolution of the solid material. In some aspects, this gas can interact with an optional surfactant and produce a foam and bubbles that cause the article 20 to press or apply pressure to the skin of the user.

In this aspect, the soluble effervescent solid material may include a sugar compound such as a mono-saccharide, di-saccharide, or poly-saccharide that has been infused with a gas that is substantially non-reactive with human skin Suitable gases for infusion into a solid material include, for example, carbon dioxide, air, nitrogen, argon, helium, other substantially inert gases, and combinations thereof. Specific examples of saccharides that can be used in accordance with the present disclosure include glucose, fructose, sucrose, lactose, maltose, dextrin, cyclodextrin, and the like, or combinations thereof. Also, a mixture of sucrose with corn syrup (containing glucose, maltose, and dextrin) can be used in accordance with this aspect of the present disclosure to produce a gas-containing effervescent material. Other examples of compounds that are capable of being prepared in such a manner as to trap pressurized gas in cells include, for example, water soluble compounds such as salts, alkali halides, and alkaline earth metal halides. Specific salts useful in the present disclosure include, for example, sodium chloride, potassium chloride, potassium bromide, lithium chloride, cesium chloride, and the like. In some aspects, the cells containing the pressurized gas have a diameter of from about 5 micrometers to about 100 micrometers.

A substantially non-reactive gas can be infused into the cells of the soluble solid material to produce an effervescent material useful in the present invention by first heating the starting material, such as a sugar, in a small amount of water until the material is dissolved. After dissolution of the material, the water is evaporated off leaving the material in a molten state. The molten material is then gasified by introducing a suitable gas, such as carbon dioxide, at a superatmospheric pressure into a sealed vessel containing the molten material. The molten material is agitated during gasification to ensure intimate contact between the molten material and the gas. Pressures of, for example, between about 50 psig (340 kPa) and about 1000 psig (6890 kPa) may be utilized to infuse the gas into the molten material. After gas infusion, the molten material is allowed to solidify while maintained in the sealed vessel to produce an effervescent material. A suitable procedure of producing a gas-containing solid material is set forth in U.S. Pat. No. 4,289,794 to Kleiner et al., which is incorporated herein by reference in a manner that is consistent herewith. The above procedure can produce solid effervescent materials containing cells of pressurized gas from about 50 psig (340 kPa) to about 900 psig (6200 kPa) which, when exposed to urine, complex fluids or other body exudates, allow the release of the trapped gas.

In some aspects, the pressure change agent comprising a gas producing material includes at least one acid and at least one base. The acid and base react together upon being wetted to produce a gas that may be, for example, carbon dioxide gas. The exact gas produced by the gas producing system is not critical, so long as the gas produced is substantially non-harmful to the skin of the wearer.

In some aspects, the stimulation material 80 can be a gas-generating material that includes a polymeric acid and a complementary base, resulting in an acid-base reaction. Suitable acidic polymers should be readily water soluble or water-wettable. Examples of suitable polymeric acids include, but are not limited to, polyacrylic acids, polystyrene phosphorus acids, and the like. In some aspects, the polymeric acid can be a "bidentate" or higher order acid. By "bidentate or higher order" it is meant that the polymeric acid has more than one acid group in its smallest polymer building block. This can be easily understood when one compares ascorbic acid to tartronic acid (two acid groups) and citric acid (three acid groups). In some aspects, the polymeric acids may be a dendrimer or the like where the dendrimer's surface and interior are fully functionalized with acid groups.

Other examples of suitable acids include, but are not limited to, acetic acid, lactic acid, amino acid, ascorbic acid, glyolic acid, salicylic acid, tartaric acid, citric acid, EDTA, tartronic acid, polyacrylic acid, maleic acid, phosphonic acid, and the like. Some non-limiting examples of polymeric acids are presented below:

Examples of simple polymeric acids include:

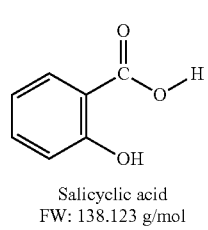

Salicyclic acid
FW: 138.123 g/mol

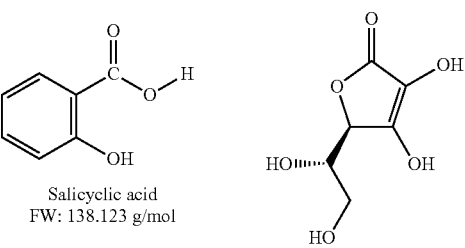

Vitamin C or Ascorbic acid

Examples of dicarboxylic polymeric acids include:

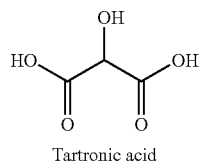

Tartronic acid

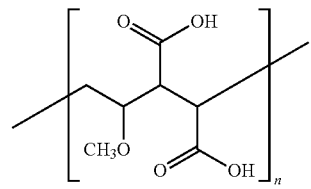

Poly(methyl vinyl ether-alt-maleic acid)
average $M_w$ ~216,000 by LS, average
$M_n$ ~80,000, powder

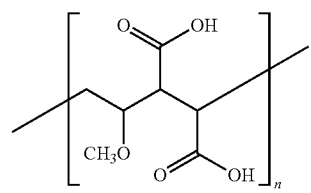

Poly(methyl vinyl ether-alt-maleic acid)
average $M_w$ ~1,980,000 by LS, average
$M_n$ ~960,000 powder Examples of tricarboxylic polymeric acids include:

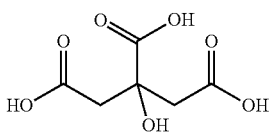

Citric acid

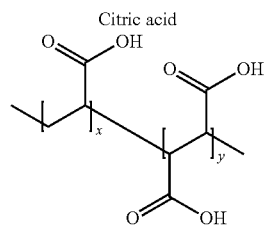

Poly(acrylic acid-co-maleic acid) solution $M_w$ 3,000, 50 wt. % in $H_2O$

Examples of polyacrylic acids include:

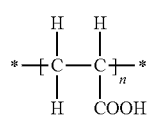

Poly(acrylic acid) average $Mw$ ~ 72 (monomer)

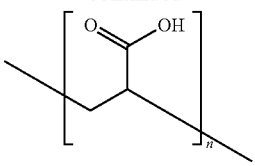

Poly(acrylic acid) average $M_w$ ~1,800

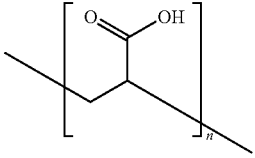

Poly(acrylic acid) average $M_w$ ~450,000

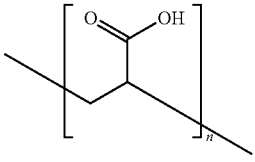

Poly(acrylic acid) average $M_w$ ~1,250,000

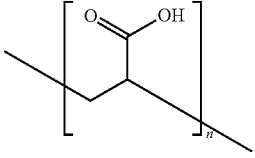

Poly(acrylic acid) average $M_w$ ~3,000,000

An example of dendrimeric acids includes:

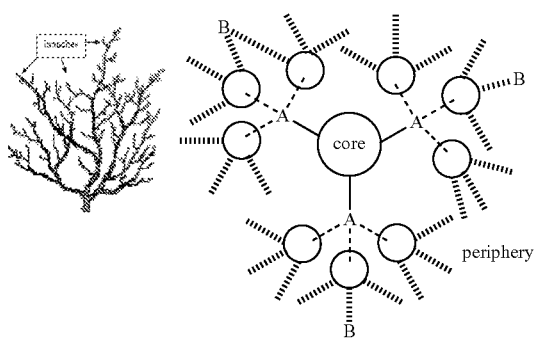

An example of strong polymeric acids includes:

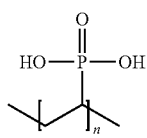

Poly(vinylphosphonic acid)

As referenced above, the acid-base reaction also includes a base, and can also include amphoteric substances that can react as either an acid or a base. For example, sodium bicarbonate (an amphoteric compound) has a pKa of 6.3 in water and causes aqueous solutions to be mildly alkaline. The reaction of sodium bicarbonate and an acid (e.g., acetic acid) results in a salt and carbonic acid, which readily decomposes to carbon dioxide and water.

In some aspects, it may be desirable to maximize the bicarbonate loading. For example, some non-limiting examples can include the following:

Tartaric acid and other cost effective dicarboxylic acids (two acidic groups)
Citric acid and other cost effective tricarboxylic acids (three acidic groups)
EDTA (four acidic groups)
Polymeric acids (may get equivalent two acidic groups like dicarboxylic acids)

In some aspects, it may be desirable to control the pH by molar ratios. To demonstrate, a non-limiting example of baking soda will be used. For purposes of example only, a complete reaction between baking soda and acids with a final pH of approximately 7 will be assumed (although it is understood that a slight excess of the base may be preferred for maximum carbon dioxide generation).

Baking Soda:Acid Molar Ratios
    1.05:1
    1.100:1
    1.25:1
Monodentate Acid vs. Baking Soda
    1:1 ratio
Bidentate Acid vs. Baking Soda
    1:1 ratio if only one acid group reacts
    0.5 (acid):1 ratio if two acid groups react
Tridentate Acid vs. Baking Soda
    1:1 ratio if only one acid group reacts
    0.5 (acid):1 ratio if two acid groups react
    0.33 (acid):1 ratio if three acid groups react
Tetradentate acid vs. baking soda
    1:1 ratio if only one acid group reacts
    0.5 (acid):1 ratio if two acid groups react
    0.33 (acid):1 ratio if three acid groups react
    0.25 (acid):1 ratio if four acid groups react In some aspects, the stimulation material 80 can be encapsulated in an aqueous-soluble shell material prior to introduction into the signal element 125. For example, if the signal element 125 includes an acid and a base, the acid and the base may be separately encapsulated in a soluble encapsulation material to keep the components separated until wetted. Alternatively, the acid and base components may be encapsulated together if reactivity between the acid and the base in the absence of an aqueous liquid is not a concern. An optional surfactant can also be separately encapsulated, or may be encapsulated with the acid and/or the base in this example. It is understood that encapsulation may be used with other types of stimulation materials described herein.

The shell material used for encapsulation may be suitably constructed of a material such that it will release the encapsulated material upon contact with aqueous liquids such as urine, complex fluids or other body exudates. The aqueous liquids can cause the shell material to solubilize, disperse, swell, or disintegrate, or the shell material may be permeable such that it disintegrates or discharges the encapsulated material upon contact with the aqueous liquids. Suitable shell materials include cellulose-based polymeric materials (e.g., ethyl cellulose), carbohydrate-based materials (e.g., starches and sugars) and materials derived therefrom (e.g., dextrins and cyclodextrins) as well as other materials compatible with human tissues.

The shell thickness may vary depending upon the material encapsulated, and is generally manufactured to allow the encapsulated component to be covered by a thin layer of encapsulation material, which may be a monolayer or thicker laminate, or may be a composite layer. The layer should be thick enough to resist cracking or breaking of the shell during handling or shipping of the product or during wear which would result in breakage of the encapsulating material. The shell material should also be constructed such that humidity from atmospheric conditions during storage, shipment, or wear will not cause a breakdown of the microencapsulation layer.

As described above, one problem with previous articles incorporating a stimulation material is that when insulted by a liquid, the effect of the stimulation material tends to be relatively short. In other words, when utilizing stimulation materials without more, the stimulating effect begins immediately upon liquid insult and its efficacy is diminished rapidly, often prior to the end of the first liquid insult of the article, such as within the first minute. As a result, the effectiveness of signaling the wearer is less than desired. In addition, in some cases, excessive quantities of the expensive stimulation material must be used in an attempt to extend the stimulating effect, which results in high manufacturing costs. Surprisingly, it has been discovered that incorporating the stimulation material into a polymeric buffering film comprising a water-soluble base polymer, and optional additives, can delay the time scale to start the stimulating effect and/or to maximize the stimulating effect once a liquid insult has begun. Accordingly, the combination of the water-soluble polymeric buffering film 140 and the stimulation material 80 provide the signal element 125 of the present invention.

To illustrate, in a particular aspect where the stimulation material 80 is a temperature change agent in the form of a cooling agent, a drop in the temperature of the product when insulted can be from about 37° C. to about 32° C., and further to about 27° C. for improved effectiveness, particularly with a preoccupied wearer. The temperature change can suitably last for at least 30 minutes, such as at least 20 minutes, or at least 10 minutes, or at least 5 minutes, or between 5 and 30 minutes or between 5 and 20 minutes for improved performance. In some aspects, the temperature change can desirably be noticeable over multiple aqueous liquid insults. For example, the signal element surface can exhibit a stimulation effect during at least two aqueous insults of the absorbent article 20, such as at least three, or at least four aqueous insults of the absorbent article 20 by a user. One method for measuring the stimulation effect over multiple insults is with the Aqueous Insult Procedure.

In some particular aspects, water-soluble polymers suitable for the water-soluble polymeric buffering films 140 include, but are not limited to, polyethylene oxide (PEO); polyethylene glycol (PEG); polyviny alcohol(PVOH); water-soluble starch derivatives such as starch ethers, carboxymethyl starch, cationic starch, hydroxyalkyl starch, and the like, for example hydroxyethyl starch, hydroxypropyl starch and hydroxybutyl starch; water-soluble cellulose derivatives such as cellulose ethers, hydroxyalkyl cellulose, e.g. hydroxyethyl cellulose, hydroxypropyl cellulose, methylcellulose, methyl propyl cellulose, carboxymethyl cellulose, and the like; polyacrylic acid; polyvinylmethyl ether; carrageenan; water-soluble alkyd resins; or the like, and combinations thereof. In addition, ethylene vinyl acetate copolymer (EVA) can be optionally utilized to control the water solubility of the polymer. In desirable aspects, the water-soluble polymeric buffering film 140 is present in the form of a carrying substrate for the stimulation material 80.

In desirable aspects, the polymeric buffering film 140 is in the form of a film or sheet-like layer. Thus, the signal element 125 is also in the form of a film or sheet-like layer. Accordingly, the signal element 125 can be present in the article 20 as a single layer or as multiple layers, such as strips. Further, the film or sheet-like layer can have any desirable shape as would be well known to those skilled in the art.

In some aspects, the water-soluble polymeric buffering film 140 can include other optional additives such as a pH adjuster and/or a plasticizer. For example, suitable plasticizers include, but are not limited to, polyhydroxy organic compounds such as glycerin and low molecular weight polyolefinic glycols such as polyethylene glycol (PEG) of molecular weight ranges from about 200 to about 10,000. The amount of plasticizer relative to the weight of the polymeric buffering film 140 can range from 0 to about 75% by weight of the plasticizer to the weight of the polymeric buffering film 140, such as from about 5% to about 60% or from about 10% to about 40% by weight of the polymeric buffering film 140 for improved performance.

To construct the signal element 125 of the present invention, the stimulation material 80 is incorporated into and/or onto the water-soluble polymeric buffering film 140. Incorporating the stimulation materials 80 into the water-soluble polymeric buffering film 140 can be accomplished by any suitable method well-known to those skilled in the art. For example, the stimulation materials 80 can be added directly into the water-soluble polymeric buffering film 140 prior to the film solidifying, such as through an extrusion process, or by melting at least portions of the film into a molten state and then adding the stimulation materials 80 to the molten portion. Accordingly, the polymeric buffering film 140 of the present invention is thermoplastic in nature. In another example, the stimulation materials 80 can be attached to the water-soluble polymeric buffering film 140 via an adhesive. In still another example, at least portions of the water-soluble polymeric buffering film 140 can be melted into a molten state and the stimulation material 80 can be sprayed onto the film. In still another example, the stimulation materials 80 can be compressed into the water-soluble polymeric buffering film 140. Other methods for incorporating the stimulation materials 80 with the water-soluble polymeric buffering film 140 will be readily apparent to those skilled in the art.

The signal element 125 as illustrated in the figures is generally rectangular. However, as noted above, the signal element 125 can have any of a number of shapes. In some aspects, the signal element 125 can be attached in an absorbent article 20, such as to an absorbent core, a surge layer and/or a topsheet for example, by bonding means known in the art, such as ultrasonic, pressure, adhesive, aperturing, heat, sewing thread or strand, autogenous or self-adhering, or the like, and combinations thereof. In other aspects, the signal element 125 may be free-floating within the article.

Figure 10:
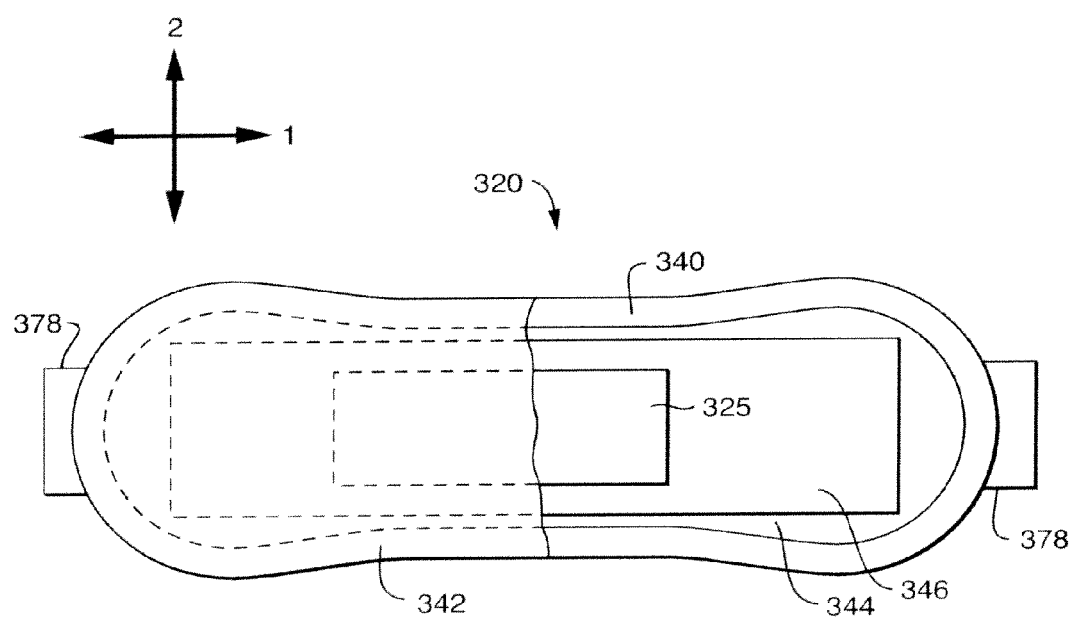
FIG. 10 is a feminine care pad having a signal element of the present invention.

While a training pant has been described above, it is understood that the signal element of the present invention can be suitable for other personal care absorbent articles. For example, FIG. 10 shows an absorbent article 220 in the form of a feminine care pad having a topsheet 242, a backsheet 240, an absorbent core 244, a surge layer 246 and a peel strip 278. The absorbent article 220 further comprises a separate signal element 225 disposed between the topsheet 242 and the surge layer 246.

The present invention may be better understood with reference to the following examples.

EXAMPLES

Example 1

In the following examples, signal elements were produced by casting polymeric buffering films incorporating stimulation materials. The stimulation materials were incorporated with the polymeric buffering film by dry blending stimulation materials with base polymer particles, and then introducing the blend into the feed throat of a twin screw extruder by a gravimetric feeder. In some instances, additional additives were also added to the extruder, either at the feed throat by a feeder or downstream to the melt of polymer in the extruder through a side feeder or by pump in the case of liquid. The extruder used was a THERMO PRISM USALAB 16 twin screw extruder (available from Thermo Electron Corporation, having a place of business located in Stone, England).

The melt blending and film extrusion were made in the same process, but could be done separately by making pellets first and then extruded into a cast or blown film. The extruder had 11 zones, numbered consecutively 1-11 from the feed hopper to the die. The specific polymers and stimulation materials, as well as any additional additives, can be seen in Tables 1-3 below. The extrusion conditions for the signal member samples comprising PEO and xylitol included the following:

Temperature (zones 1-5)=75° C.
Temperature (zones 6-11)=80° C.
Extrusion Temperature of the polymeric film at the Die=60° C.
Screw Speed=60-100 rpm The extrusion conditions for the signal member samples comprising PEO and urea included the following:
Temperature (zones 1-6)=80° C.
Temperature (zones 7-11)=90° C.
Extrusion Temperature of the polymeric film at the Die=90° C.
Screw Speed=80-100 rpm The resulting molten polymer containing the stimulation material and any other additives was cast into films having a thickness of approximately 0.3 mm, and allowed to set. The samples were then tested for physical properties. More specifically, 20 grams of tap water having a pH of 7.53 was provided in a container and the temperature was recorded. Then, 1.0 gram of each sample was placed into the tap water such that the sample was completely submerged. The change in temperature of the tap water was then measured after particular time intervals, and the pH of the tap water solution after 5 minutes was noted. The results can be seen in Table 1 below:

TABLE 1

| Example | Polymer | Stimulation Material | Solubility Controller | pH Adjuster | Plasticizer | Solution Temperature Change (° C.) | pH of water |
|---|---|---|---|---|---|---|---|
| Comparative Sample 1 | PVOH 70 wt % | | EVA 10 wt % | | Glycerin 20 wt % | −0.1 at 5 minutes | 7.52 |
| Comparative Sample 2 | PVOH 90 wt % | | | | Glycerin 10 wt % | −0.1 at 5 minutes | 7.58 |

TABLE 1-continued

| Example | Polymer | Stimulation Material | Solubility Controller | pH Adjuster | Plasticizer | Solution Temperature Change (° C.) | pH of water |
|---|---|---|---|---|---|---|---|
| Sample 3 | PVOH 49 wt % | Ammonium Chloride 30 wt % | EVA 7 wt % | | Glycerin 14 wt % | −0.4 at 5 minutes | 5.90 |
| Sample 4 | PVOH 49 wt % | $MnCl_2$ 30 wt % | EVA 7 wt % | | Glycerin 14 wt % | +0.6 at 5 minutes | 7.33 |
| Sample 5 | PEO 45 wt % | Xylitol 50 wt % | | | Glycerin 5 wt % | −0.6 at 5 minutes; −0.5 at 10 minutes | 8.54 |
| Sample 6 | PEO 37.5 wt % | Urea 50 wt % | EVA 5 wt % | Polyacrylic Acid 2.5 wt % | Glycerin 5 wt % | −1.0 at 5 minutes; −0.9 at 10 minutes | 5.74 |
| Sample 7 | PEO 32.5 wt % | Urea 50 wt % | EVA 5 wt % | Polyacrylic Acid 2.5 wt % | Glycerin 10 wt % | −1.5 at 5 minutes; −0.8 at 10 minutes | 5.85 |

Next, 40 mm by 40 mm pieces of selected samples were cut and the temperature of each sample was measured using an INFRARED THERMOMETER Model 39650-20 IR gun (available from Cole-Parmer Instruments, having a place of business located in Chicago, Ill., U.S.A.). Each cut sample was then completely submerged into tap water having a temperature of 23° C. for 10 seconds. The sample was removed from the water and the surface temperature of the wetted film was immediately measured using the IR gun to determine the surface temperature change of the wet sample versus the dry sample. The results can be seen in Table 2 below:

TABLE 2

| Example | Polymer | Stimulation Material | Solubility Controller | pH Adjuster | Plasticizer | Surface Temperature Change of Sample (° C.) |
|---|---|---|---|---|---|---|
| Comparative Sample 2 | PVOH 90 wt % | | | | Glycerin 10 wt % | 0 |
| Sample 3 | PVOH 49 wt % | Ammonium Chloride 30 wt % | EVA 7 wt % | | Glycerin 14 wt % | −2.8 |
| Sample 5 | PEO 45 wt % | Xylitol 50 wt % | | | Glycerin 5 wt % | −5.6 |
| Sample 6 | PEO 37.5 wt % | Urea 50 wt % | EVA 5 wt % | Polyacrylic Acid 2.5 wt % | Glycerin 5 wt % | −5.2 |
| Sample 7 | PEO 32.5 wt % | Urea 50 wt % | EVA 5 wt % | Polyacrylic Acid 2.5 wt % | Glycerin 10 wt % | −5.1 |

Next, 40 mm by 40 mm pieces of selected samples were cut and then completely submerged into tap water having a temperature of 23° C. for 10 seconds. Each sample was removed from the water and immediately placed on the skin of the tester. Then after 5 minutes, the surface temperature of the wetted film and the temperature of the tester's skin located approximately 5 cm from the wetted film was measured using the IR gun to determine the continuing stimulation effect of the sample when adjacent the body. The results can be seen in Table 3 below:

TABLE 3

| Example | Polymer | Stimulation Material | Solubility Controller | pH Adjuster | Plasticizer | Sample Surface Temperature Change vs. Skin (° C.) |
|---|---|---|---|---|---|---|
| Comparative Sample 1 | PVOH 70 wt % | | EVA 10 wt % | | Glycerin 20 wt % | 0 |
| Comparative Sample 2 | PVOH 90 wt % | | | | Glycerin 10 wt % | 0 |
| Sample 3 | PVOH 49 wt % | Ammonium Chloride 30 wt % | EVA 7 wt % | | Glycerin 14 wt % | −2.2 |
| Sample 5 | PEO 45 wt % | Xylitol 50 wt % | | | Glycerin 5 wt % | −4.0 |
| Sample 6 | PEO 37.5 wt % | Urea 50 wt % | EVA 5 wt % | Polyacrylic Acid 2.5 wt % | Glycerin 5 wt % | −3.9 |
| Sample 7 | PEO 32.5 wt % | Urea 50 wt % | EVA 5 wt % | Polyacrylic Acid 2.5 wt % | Glycerin 10 wt % | −5.1 |

Tables 1-3 show that the combination of stimulation material and a polymeric buffering film provide a viable signal element for the present invention. Table 3 further shows that the signal element of the present invention continues to provide a stimulating effect even after 5 minutes of being in contact with a human body, thus showing the ability of the signal element to be effective over multiple aqueous insults.

Example 2

In the following examples, signal elements were produced by casting polymeric buffering films and incorporating stimulation materials as described in Example 1. The specific polymers, stimulation materials and any additional additives can be seen in Table 4 below. The samples were then tested for physical properties. More specifically, 20 grams of filtered water having a pH of 6.67 was provided in an insulated container and the temperature was recorded. The filtered water was tap water that had been run through a MILLIPORE lab filter, available from Millipore, having a place of business located in Billerica, Mass., U.S.A. Particular amounts of each signal element sample were placed into the water and allowed to dissolve. The change in temperature of the filtered water was then measured after particular time intervals, and the final pH of the filtered water after dissolution was noted. The results can be seen in Table 4 below:

TABLE 4

| Example | Sample Wt. and Composition | Water Temperature Drop (° C.) vs. Time | pH | Notes |
|---|---|---|---|---|
| Comparative Sample 8 | Filtered Water only | 0.55 (1 min), 0 (3 min), 0 (5 min) | 6.67 | |
| Comparative Sample 9 | 0.5 g Xylitol | −0.55 (1 min), −0.61 (2 min), −0.61 (3 min), −0.55 (5 min), −0.33 (20 min), 0 (30 min) | 6.62 | Dissolved in less than 1 minutes |
| Comparative Sample 10 | 0.5 g Urea | −1.10 (1 min), −1.16 (2 min), −1.10 (3 min), −0.99 (5 min), −0.94 (10 min) | 7.09 | Dissolved in less than 1 minute |
| Comparative Sample 11 | 1.0 g<br>25 wt % Coform*<br>75 wt % sobitol | −0.55 (1 min), −0.50 (2 min), −0.44 (3 min), −0.17 (5 min), −0.11 (10 min) | 6.50 | Maximum Temperature dropped in the 1st minute |
| Sample 12 | 1.0 g<br>45 wt % PEO<br>5 wt % Glycerin<br>50 wt % Xylitol | −0.17 (1 min), −0.17 (2 min), −0.22 (3 min), −0.33 (5 min), −0.39 (7 min), −0.50 (10 min), −0.44 (15 min), −0.39 (20 min), −0.28 (30 min) | 9.53 | Slowly dissolved within 30 minutes |
| Sample 13 | 1.0 g<br>52.5 wt % PEO<br>2.5 wt % PAA<br>5 wt % EVA<br>10 wt % Glycerin<br>50 wt % Urea | −0.39 (1 min), −0.50 (2 min), −0.77 (3 min), −0.88 (4 min), −0.83 (5 min), −0.77 (10 min), −0.39 (20 min) | 4.56 | Dissolved after 20 min |

*The coform fabric comprised 67 wt % polypropylene meltblown fibers and 33 wt % pulp (cellulosic) fibers.

The Tables show that the signal element of the present invention can be designed to delay the stimulation material from quickly dissolving, and can maximize the stimulant effect after insult, resulting in a longer cooling effect versus pure stimulation materials and those combined with coform. For example, referring to Table 4, it can be seen that the pure stimulation materials of Comparative Samples 9 and 10 completely dissolved during the first minute, whereas Sample 12 of the invention took 30 minutes to dissolve and Sample 13 of the invention took 20 minutes to dissolve. It can also be seen that the maximum cooling effect of Comparative Sample 10 comprising urea occurred in the first 1-3 minutes, whereas the maximum cooling effect of Sample 13 did not occur until between 3 and 10 minutes. It can further be seen that the coform composite of Comparative Sample 11 reached its maximum temperature change during the first minute, whereas Samples 12 and 13 of the invention did not reach maximum temperature change until well after insult. In addition, it can be seen that even at 30 minutes and 20 minutes for Samples 12 and 13 respectively, the signal element continued to provide a cooling effect.

It will be appreciated that details of the foregoing examples, given for purposes of illustration, are not to be construed as limiting the scope of this invention. Although only a few exemplary embodiments of this invention have been described in detail above, those skilled in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the desirable embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

What is claimed is:

1. An absorbent article comprising a signal element;
  wherein the signal element has a body-facing surface, a garment-facing surface, a longitudinal direction, a transverse direction and a z-direction;
  wherein the signal element comprises a water-soluble polymeric buffering film incorporating a stimulation material, wherein the stimulation material is a cooling agent selected from xylitol, sorbitol or urea and with a heat of solution, hydration, or reaction of −30 to −90 cal/g;
  wherein the water-soluble polymeric buffering film comprises a water-soluble base polymer selected from polyethylene oxide, polyethylene glycol or polyvinyl alcohol; and
  wherein the signal element exhibits a surface temperature change of at least +/−2° C. from a dry state at 23° C. after being completely submerged for 10 seconds in tap water having a temperature of 23° C.

2. The absorbent article of claim 1 wherein the water-soluble polymeric buffering film further comprises at least one of a plasticizer, a water-solubility control agent or a pH adjustment agent.

3. The absorbent article of claim 1 wherein the stimulation material is present in the signal element at a basis weight of 50 gsm to 2000 gsm.

4. The absorbent article of claim 1 wherein the stimulation material has a solubility of from 0.1 grams to 6 grams of material per gram of water.

5. The absorbent article of claim 1 wherein the signal element exhibits a stimulation effect for at least 5 minutes after a first aqueous insult according to the Aqueous Insult Procedure.

6. The absorbent article of claim 1 wherein the signal element exhibits a stimulation effect during at least two aqueous insults according to the Aqueous Insult Procedure.

7. The absorbent article of claim 1 wherein the signal element does not completely dissolve until between 5 minutes and 30 minutes after being completely submerged in tap water at 23° C.

8. The absorbent article of claim 1 wherein the signal element does not reach a maximum stimulation effect until at least 4 minutes after a first aqueous insult according to the Aqueous Insult Procedure.

9. An absorbent article comprising a signal element;
wherein the signal element has a body-facing surface, a garment-facing surface, a longitudinal direction, a transverse direction and a z-direction;
wherein the signal element comprises a water-soluble polymeric buffering film incorporating a stimulation material, wherein the stimulation material is a cooling agent selected from xylitol, sorbitol or urea and with a heat of solution, hydration, or reaction of −30 to −90 cal/g;
wherein the water-soluble polymeric buffering film comprises a water-soluble base polymer selected from polyethylene oxide, polyethylene glycol or polyvinyl alcohol; and
wherein the signal element exhibits a stimulation effect over at least two aqueous insults according to the Aqueous Insult Procedure.

10. The absorbent article of claim 9 wherein the water-soluble base polymer is selected from polyethylene oxide, polyethylene glycol or polyvinyl alcohol.

11. The absorbent article of claim 9 wherein the water-soluble polymeric buffering film further comprises at least one of a plasticizer, a water-solubility control agent or a pH adjustment agent.

12. The absorbent article of claim 9 wherein the signal element exhibits a stimulation effect for at least 5 minutes after a first aqueous insult according to the Aqueous Insult Procedure.

13. The absorbent article of claim 12 wherein the signal element exhibits a stimulation effect for at least 20 minutes after a first aqueous insult according to the Aqueous Insult Procedure.

14. The absorbent article of claim 9 wherein the signal element does not completely dissolve until between 5 minutes and 30 minutes after being completely submerged in tap water at 23° C.

* * * * *